United States Patent
Vicente

(10) Patent No.: US 7,267,990 B2
(45) Date of Patent: Sep. 11, 2007

(54) CHELATION OF CHARGED AND UNCHARGED MOLECULES WITH PORPHYRIN-BASED COMPOUNDS

(75) Inventor: Maria da Graça Henriques Vicente, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 289 days.

(21) Appl. No.: 10/712,513

(22) Filed: Nov. 12, 2003

(65) Prior Publication Data

US 2004/0106592 A1 Jun. 3, 2004

Related U.S. Application Data

(60) Provisional application No. 60/426,612, filed on Nov. 15, 2002.

(51) Int. Cl.
  *G01N 33/00* (2006.01)
  *A61K 31/555* (2006.01)
  *A61K 31/409* (2006.01)
  *A61K 31/4178* (2006.01)

(52) U.S. Cl. .................. 436/91; 436/73; 436/96; 540/145; 514/64; 514/185; 514/397; 514/410

(58) Field of Classification Search .......... 436/91, 436/96, 73, 77, 81, 84; 540/145; 568/1, 568/3–6; 514/64, 185, 397, 410
See application file for complete search history.

(56) References Cited

U.S. PATENT DOCUMENTS

| 4,959,356 | A | * | 9/1990 | Miura et al. .......... 424/1.81 |
| 5,284,831 | A | * | 2/1994 | Kahl et al. ............... 514/21 |
| 5,877,165 | A | * | 3/1999 | Miura et al. ............. 514/64 |
| 5,955,586 | A | * | 9/1999 | Sessler et al. ............ 534/15 |
| 6,566,517 | B2 | * | 5/2003 | Miura et al. ........... 540/145 |
| 6,759,403 | B2 | * | 7/2004 | Miura et al. ........... 514/185 |
| 6,951,640 | B2 | * | 10/2005 | Miura et al. .......... 424/1.65 |
| 7,067,653 | B2 | * | 6/2006 | Vicente et al. ........ 540/145 |

FOREIGN PATENT DOCUMENTS

WO    WO 01/85736    11/2001

OTHER PUBLICATIONS

Barth, R. et al., "Boron Neutron Capture Therapy of Brain Tumors: An Emerging Therapeutic Modality," *Neurosurg.*, vol. 44, No. 3, pp. 433-451 (1999).

U.S. Appl. No. 60/426,612, filed Nov. 15, 2002, Vicente.

U.S. Appl. No. 60/426,062, filed Nov. 13, 2002, Vicente et al.

Allen, W. et al., "Binding of neutral substrates by calix[4]pyrroles," *J. Am. Chem. Soc.*, vol. 118, pp. 12471-12472 (1996).

Dougherty, T. et al., "Photodynamic Therapy," *J. Natl. Cancer Inst.*, vol. 90, pp. 889-905 (1998).

(Continued)

*Primary Examiner*—Maureen M. Wallenhorst
(74) *Attorney, Agent, or Firm*—John H. Runnels; Bonnie J. Davis

(57) ABSTRACT

Porphyrins containing one or more neutral or negatively-charged, closo- or nido-carborane substituents are useful as chelators. The carbon-carbon bonds linking the boron-containing groups to the porphyrin ring make the compounds highly resistant to hydrolysis. These compounds have potential for use in selective binding to specific ligands. These compounds are highly stable, soluble in water and organic solvents, and have low toxicity.

16 Claims, 16 Drawing Sheets

Scheme 1

OTHER PUBLICATIONS

Gale, P. et al., "Calix[4]pyrroles: old yet new anion-binding agents," *J. Am. Chem. Soc.*, vol. 118, pp. 5140-5141 (1996).

Hsi, R. et al., "Photodynamic Therapy in the Treatment of Cancer. Current State of the Art," *Drugs*, vol. 57, pp. 725-734 (1999).

Lauceri, R. et al., "Interactions of Anionic Caboranylated Porphyrins with DNA," *J. Am. Chem. Soc.*, vol. 123, pp. 5835-5836 (2001).

Madema, A. et al., "Synthesis of a porphyrin-labelled carboranyl phosphate diester: a potential new drug for boron neutron capture therapy of cancer," *Chem. Commun.*, pp. 1784-1785 (2002).

Sessler, J. et al., "Anion binding: a new direction in porphyrin-related research," *Pure & Appl. Chem.*, vol. 65, pp. 393-398 (1993).

Sessler, J. et al., "Anion binding: self-assembly of polypyrrolic macrocycles," *Angew. Chem. Int. Ed. Engl.*, vol. 35, pp. 2782-2785 (1996).

Vicente, M. et al., "First Structural Characterization of a Covalently Bonded Porphyrin-Carborane System," *Chem. Commun.*, pp. 483-484 (2001).

Vicente, M., "Porphyrin-based sensitizers in the dectection and treatment of cancer: recent progress," *Curr. Med. Chem.*, vol. 1, pp. 175-194 (2001).

Vicente, M. et al., "Syntheses and preliminary biological studies of four *meso*-tetra[(*nido*-carboranylmethyl)phenyl]prophyrins," *Bioorganic & Medicianl Chem.*, vol. 10, pp. 481-492 (2002).

Vicente, M. et al., "Syntheses of carbon-carbon linked carboranylated porphyrins for boron neutron capture therapy of cancer," *Tetr. Lett.*, vol. 41, pp. 7623-7627 (2000).

Vicente, M. et al., "Synthesis, dark toxicity and induction of in vitro DNA photodamage by a tetra(4-*nido*-carboranyl)porphyrin," *J. Photochemistry and Photobiology*, vol. 68, pp. 123-132 (2002).

\* cited by examiner

Scheme 2

Scheme 4

Scheme 5

53

54

CHELATION OF CHARGED AND UNCHARGED MOLECULES WITH PORPHYRIN-BASED COMPOUNDS

The benefit of the filing date of provisional application Ser. No. 60/426,612, filed Nov. 15, 2002, is claimed under 35 U.S.C. § 119(e).

This invention pertains to the chelation of charged and uncharged molecules.

Many of the current, commercially available receptors for molecular recognition are difficult and expensive to synthesize, and are typically only obtained in low yield. There is an unfilled need for binding agents that are easy to synthesize, and that are selective for specific substrates, both charged and uncharged.

J. Sessler et al., "Anion binding: a new direction in porphyrin-related research," *Pure & Appl. Chem.*, vol. 65, pp. 393-398 (1993) discloses the use of certain porphyrin or porphyrin-type compounds to chelate certain anionic substrates.

P. Gale et al., "Calix[4]pyrroles: old yet new anion-binding agents," *J. Am. Chem. Soc.*, vol. 118, pp. 5140-5141 (1996) discloses the use of certain octaalkylporphyrinogens as binding agents for certain anionic species.

W. Allen et al., "Binding of neutral substrates by calix[4]pyrroles," *J. Am. Chem. Soc.*, vol. 118, pp. 12471-12472 (1996) discloses the use of certain porphyrin or porphyrin-type compounds to bind certain neutral substrates, both in the solid state and in solution.

J. Sessler et al., "Anion binding: self-assembly of polypyrrolic macrocycles," *Angew. Chem. Int. Ed. Engl.*, vol. 35, pp. 2782-2785 (1996) discloses that certain zwitterionic sapphyrins and certain calix[4]pyrroles can readily self-assemble.

M. Vicente, "Porphyrin-based sensitizers in the detection and treatment of cancer: recent progress," *Curr. Med. Chem.*, vol. 1, pp. 175-194 (2001) provides a review of the use of porphyrins for cancer detection and treatment by photodynamic therapy, boron neutron capture therapy, radiation therapy, and magnetic resonance imaging.

M. Vicente et al., international patent application WO 01/85736 (2001), discloses the use of the same class of porphyrin-based compounds that are used in the present invention, but for a different purpose, namely, in boron neutron capture therapy for treatment of cancer. See also M. Vicente et al., "Syntheses and preliminary biological studies of four meso-tetra[(nido-carboranylmethyl)phenyl]porphyrins," *Bioorganic & Medicinal Chem.*, vol. 10, pp. 481-492 (2002); A. Maderna et al., "Synthesis of a porphyrin-labelled carboranyl phosphate diester: a potential new drug for boron neutron capture therapy of cancer," *Chem. Commun.*, pp. 1784-1785 (2002); M. Vicente et al., "Syntheses of carbon-carbon linked carboranylated porphyrins for boron neutron capture therapy of cancer," *Tetr. Lett.*, vol. 41, pp. 7623-7627 (2000); and M. Vicente et al., "Synthesis, dark toxicity and induction of in vitro DNA photo damage by a tetra(4-nido-carboranyl)porphyrin," *J. Photochemistry and Photobiology.* Vol. 68, pp. 123-132 (2002).

M. Vicente et al., "First Structural Characterization of a Covalently Bonded Porphyrin-Carborane System," *Chem. Commun.*, pp. 483-484 (2001) reported that the large carborane substituents significantly increase the barriers for aryl rotation in tetra(carboranylphenyl)porphyrins.

R. Lauceri et al., "Interactions of Anionic Carboranylated Porphyrins with DNA," *J. Am. Chem. Soc.*, vol. 123, pp. 5835-5836 (2001) reported that the large carborane substituents in tetra(carboranylphenyl)porphyrins influence the basicity of the inner porphyrin nitrogens and their aggregation state.

Additional Citations: R. Barth et al., *Neurosurg.*, vol. 44. pp. 433-451 (1999); T. Dougherty et al., "Photodynamic Therapy," *J. Natl. Cancer Inst.*, vol. 90, pp. 889-905 (1998); and R. Hsi et al., "Photodynamic Therapy in the Treatment of Cancer. Current State of the Art," *Drugs*, vol. 57, pp. 725-734 (1999).

To the inventor's knowledge, no prior reference has suggested that porphyrins containing nido-carborane or closo-carborane cages would be useful as chelators or specific binding agents.

I have discovered that certain carboranyl-containing porphyrin compounds, such as those disclosed in M. Vicente et al., international patent application WO 01/85736 (2001), bearing chemically stable carbon-carbon bonds between the carborane clusters and the porphyrin ring, may be used to selectively chelate or bind a variety of substrates. The large carborane substituents can significantly increase the steric barriers to aryl rotation in tetra(carboranylphenyl)porphyrins, in addition to influencing the basicity of the inner porphyrin nitrogens and their aggregation state. These carboranylporphyrins are able to effectively bind a variety of molecules and ions by: (1) coordination to a pentacoordinated or hexacoordinated metal ion such as Zn(II), Fe(III), Mn(III), Al(III), or Sn(IV) in the macrocyclic core, for example compounds 5, 6, 11, 12, 17, 18, 23, 24, 30, 31, 35, and 36; (2) electrostatic interactions with the carborane groups, for example compounds 3-6, 9-12, 15-18, 21-24, 28-31, and 33-36; and (3) interactions (such as π-π interactions) with the aromatic macrocycle, for example compounds 3-6, 9-12, 15-18, 21-24 28-31, and 33-36.

Several examples of these interactions have been experimentally observed to date. For example, observed interactions of type (1) include the following: In the solid state, depending on which other components are present during recrystallization (e.g., pyridine, methanol, picric acid, or HCl), zinc(II) carboranylporphyrins have been obtained with different axial ligands: a pyridine, a methanol, a water molecule, or chloride. Certain molecules have high affinity and selectivity for binding the zinc ion; the carborane groups modulate this specificity. In aqueous solution, both metal-free and Zn(II) complexes of nido-carboranylporphyrins have been observed to have an affinity for binding to biomolecules, such as DNA, lipoproteins, and albumin. This binding affinity can strongly influence their biological properties. More generally, binding of type (1) may include, for example, binding to ligands containing electronegative atoms such as nitrogen, oxygen, or sulfur, for example, pyridines, amines, amides, carboxylic acids, hydroxyls, thiols, sulfates, sulfides, and sulfoxides.

UV-Vis spectrophotometry has also shown that nido-carboranylporphyrins bind to serum proteins in solution.

Examples of observed interactions of type (2) include the following: The negatively charged nido-carboranyl groups have been observed to efficiently bind organic and inorganic cations, for example, sodium, potassium, and piperidinium. These complexes were prepared by ion-exchange using a Dowex 50WX2-100 resin.

Examples of observed interactions of type (3) include the following: Metal-free tetra(nido-carboranyl)porphyrins bearing the carborane cages on the para-phenyl positions have been observed to protonate at pH~7, while the regioisomers with the nido-carborane cages on the meta-phenyl positions are essentially unprotonated at pH~7. The protonated carboranylporphyrins are capable of strongly and selectively binding organic and inorganic anions, for example, phosphates, sulfates, sulfonates, carboxylates, thiolates, and alkoxides. A large number of carborane cages (e.g. 4-8, preferably 8) at the periphery of porphyrin macrocycles also make it easy to protonate the porphyrin macrocycle, due to the bulkiness and electron-withdrawing effect of the carborane cages. In the solid state diprotonated octa(closo-carboranyl)porphyrins have been identified, such as compound 28 (M=4H), that selectively bind two picrate molecules or two chloride ions.

A surprising interaction of types (1) and (2) has been observed in the solid state for Zn(II) tetra(closo-carboranyl) porphyrin compound 5. Close intermolecular contacts were inferred between the BH hydrogens of a carborane group of one porphyrin and the centrally-chelated zinc ion of another porphyrin. This interaction produced an unusual pseudo-hexacoordinated zinc porphyrin complex. (Zinc porphyrins are usually penta-coordinated).

Negatively-charged nido-carboranylporphyrins can efficiently and selectively bind positively charged molecules, as well as neutral and negatively charged molecules, by interaction with the positive macrocyclic core (upon protonation), or by axial ligation to the centrally-chelated metal ions, or both. On the other hand, closo-carboranylporphyrins can specifically bind neutral and negatively charged molecules by interaction with the positive macrocyclic core (upon protonation), or by axial ligation to the centrally-chelated metal ions, or both.

The position, nature, and distribution of the bulky carboranyl cages at the periphery of the porphyrin macrocycle affect their selectivity for substrate recognition and binding, both in organic and aqueous solutions, as well as in the solid state. Closo- and nido-carboranylporphyrins are readily protonated at the inner porphyrin core, and the resulting positively-charged or zwitterionic species can potentially bind anionic, cationic, and polar neutral substrates via electrostatic interactions. Penta- and hexa-coordinated metallocarboranylporphyrins effectively bind anionic and neutral ligands via axial coordination to the central metal cation. Hydrogen bonding, hydrophobic, and π-π interactions can further enhance binding and specificity.

Carboranylporphyrins that may be used in this invention can have varying distributions of carborane cages at the periphery of the macrocycle. The number and distribution of the carborane cages will affect the selectivity and specificity of binding.

When these carboranylporphyrins are complexed to other compounds, the UV-visible and fluorescence spectra of the latter are typically altered, particularly the visible and fluorescence spectra. These carboranylporphyrins will frequently bind more strongly than will the commercially-available, hydrogen-bonding ligands that are typically used today.

Uses for this invention include such things as removing impurities from water, environmental remediation, electronics applications, transport of ionic species generally, sensors for selective ion binding, sensors for selective substrate recognition, separation membranes, electrodes, field effect transistors, and selective binding of specific substrates in biological systems.

Specificity of binding may be modulated by selecting the number of carborane substituents, by selecting closo- or nido-carborane substituents, by selecting the metal ion in the macrocyclic core, and by selecting the position of substitution for the carborane substituents on the phenyl groups. The carboranes are electron-withdrawing groups, so in general, the more such groups that are present, the more positive charge will tend to be carried by the central metal ion—although this general tendency can be affected by the distribution and steric hindrance of the carborane groups in a particular compound. A closo-carborane cage is uncharged, but electron-withdrawing, while a nido-carborane group is negatively charged, and will bind electrostatically to cations on the periphery of the compound. Varying the metal ion in the core can alter its electropositivity, and can alter the affinity for various anions and neutral polar molecules. If the carborane groups are substituted in the para position on the phenyl group, then they act primarily as centers of negative charge, but do not tend to form a central cavity. If the carborane groups are substituted in the meta position, then they tend to form a cavity that can hold a ligand. In the meta position, the phenyl groups are still free to rotate; although the energy barrier to rotation is larger than for the para-phenyl substituted carboranylporphyrins. If the carborane groups are substituted in the ortho position, then they tend to form a still tighter cavity for the ligand. With ortho substitution, the phenyl groups are sterically hindered from rotating, and atropisomers can thereby form (e.g. up, up, up, up—or up, down, up, down—or up, up, up, down—or up, up, down, down). A mixture of atropisomers will generally be the product of syntheses of these compounds; different atropisomers may be separated from one another by means known in the art, e.g., chromatographically.

A nido-carborane group is depicted as structure 51 in FIG. 13(a). A closo-carborane group is depicted as structure 61 in FIG. 13(b).

Examples of active compounds include the compounds depicted as structures 52, 53, and 54 in FIGS. 13(c)-(e). In these structures, M may be a metal ion, preferably a penta-coordinated or hexacoordinated metal ion such as Zn(II), Fe(III), Mn(III), Al(III), or Sn(IV), or it may be 2H, the last resulting in a metal-free macrocycle.

The negative charges lie primarily in the boron clusters. The carbon-carbon bonds linking the boron-containing groups to the porphyrin ring make the compounds highly resistant to hydrolysis. By contrast, most prior work with boron-containing porphyrin compounds has relied on ester linkages, which are susceptible to hydrolysis in vivo.

These compounds have low toxicity to normal mammalian cells.

Figure 1:
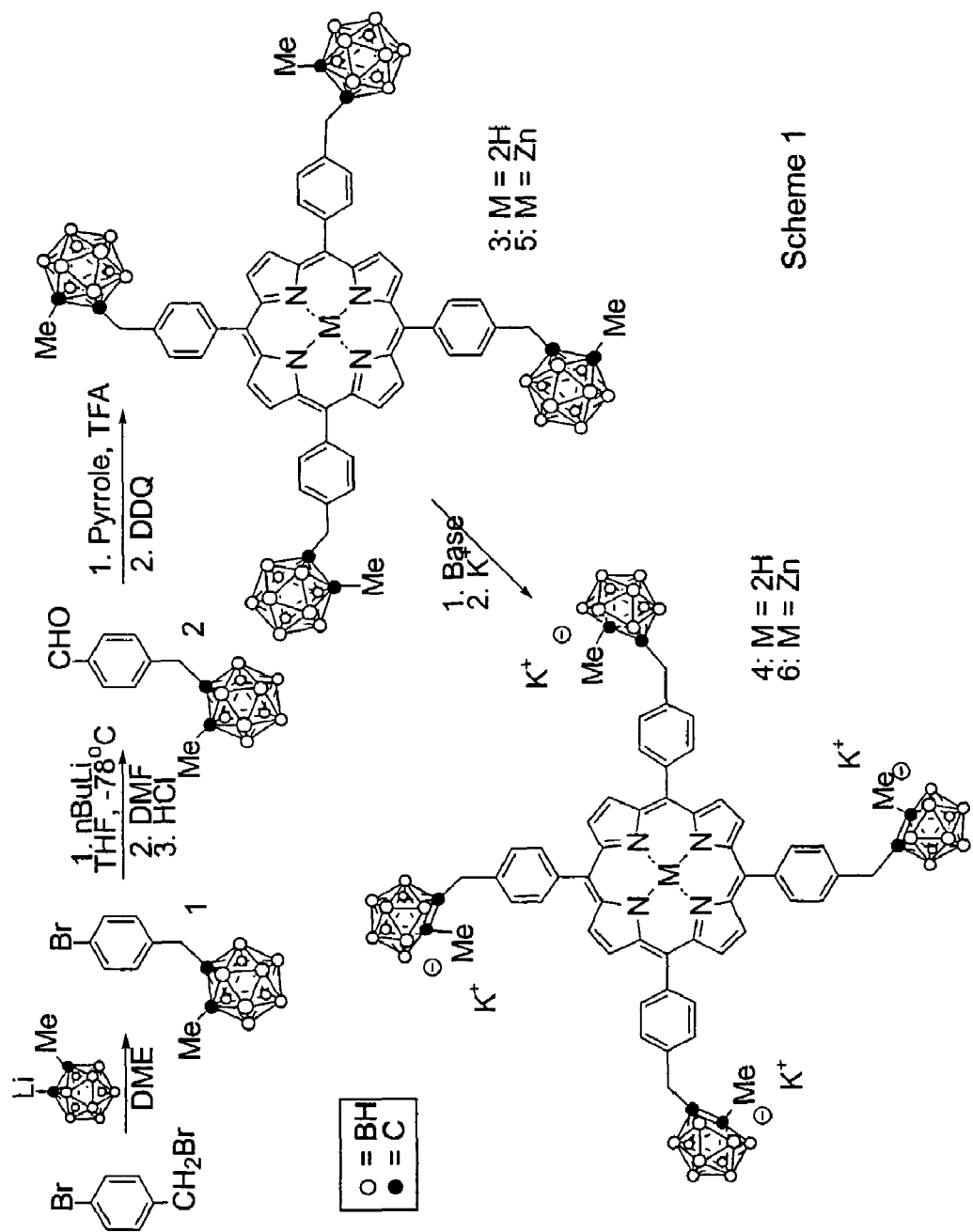
FIG. 1 (Scheme 1) depicts the synthesis of compounds 1-6.
Figure 2:
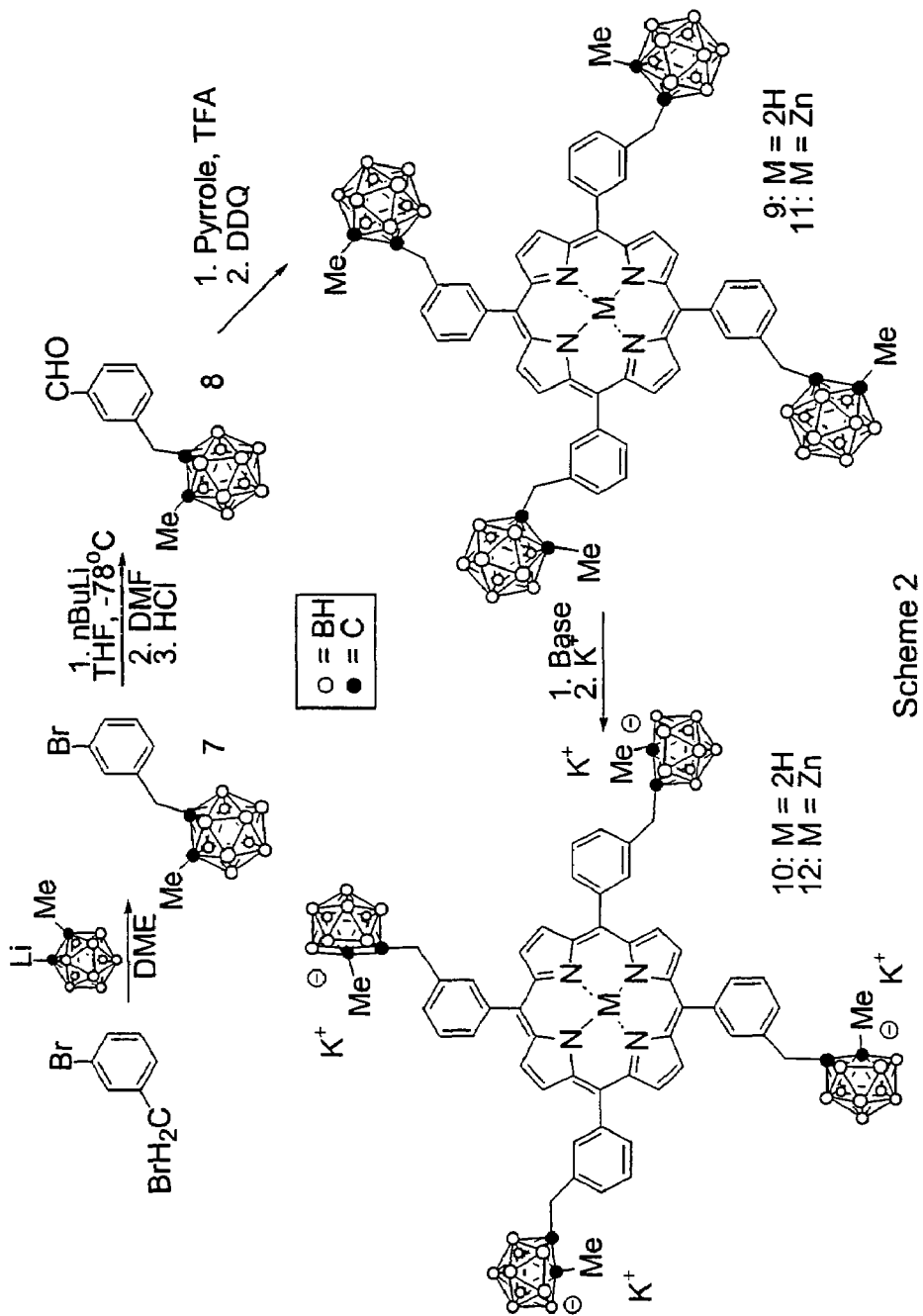
FIG. 2 (Scheme 2) depicts the synthesis of compounds 7-12.
Figure 3:
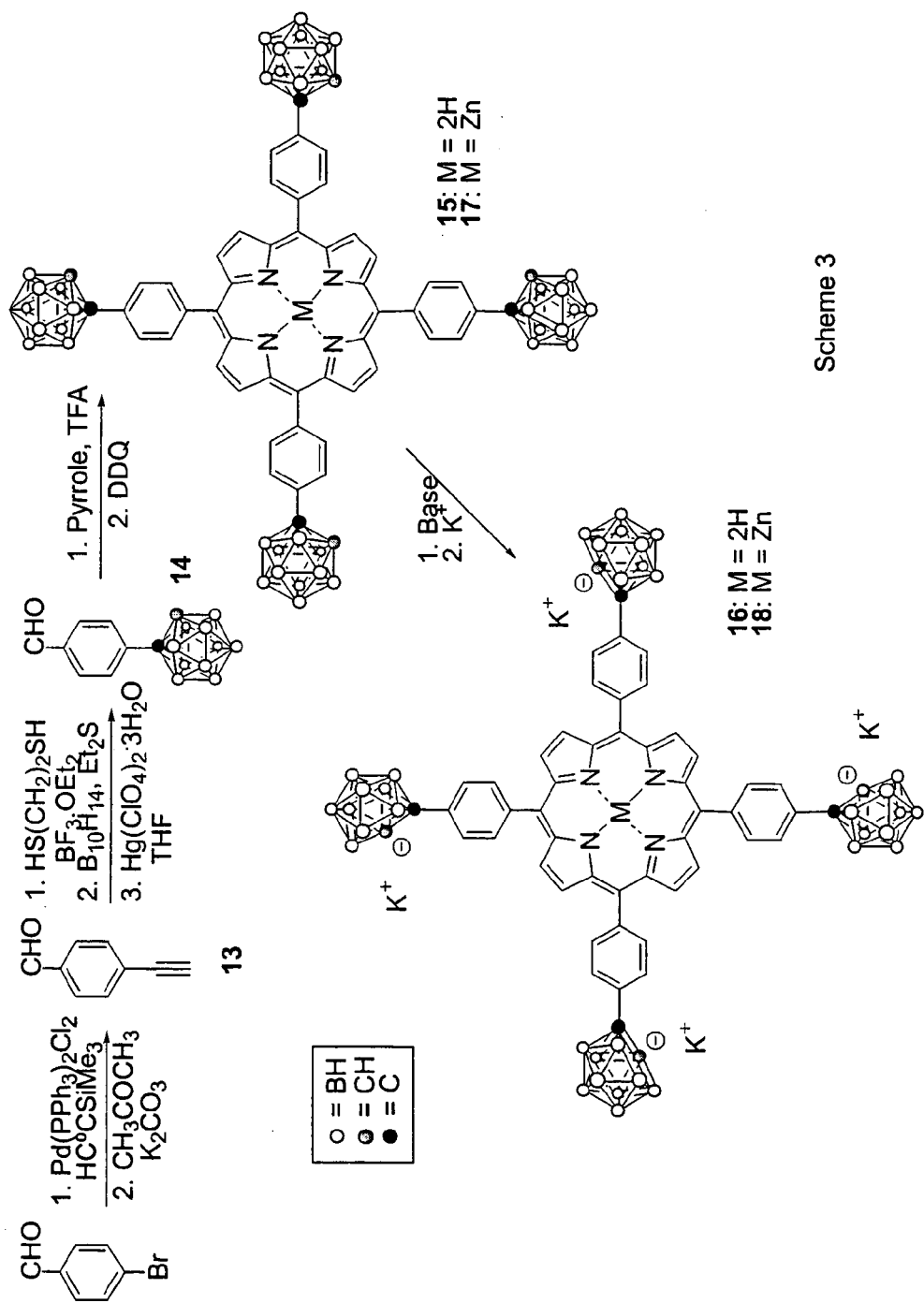
FIG. 3 (Scheme 3) depicts the synthesis of compounds 13-18.
Figure 4:
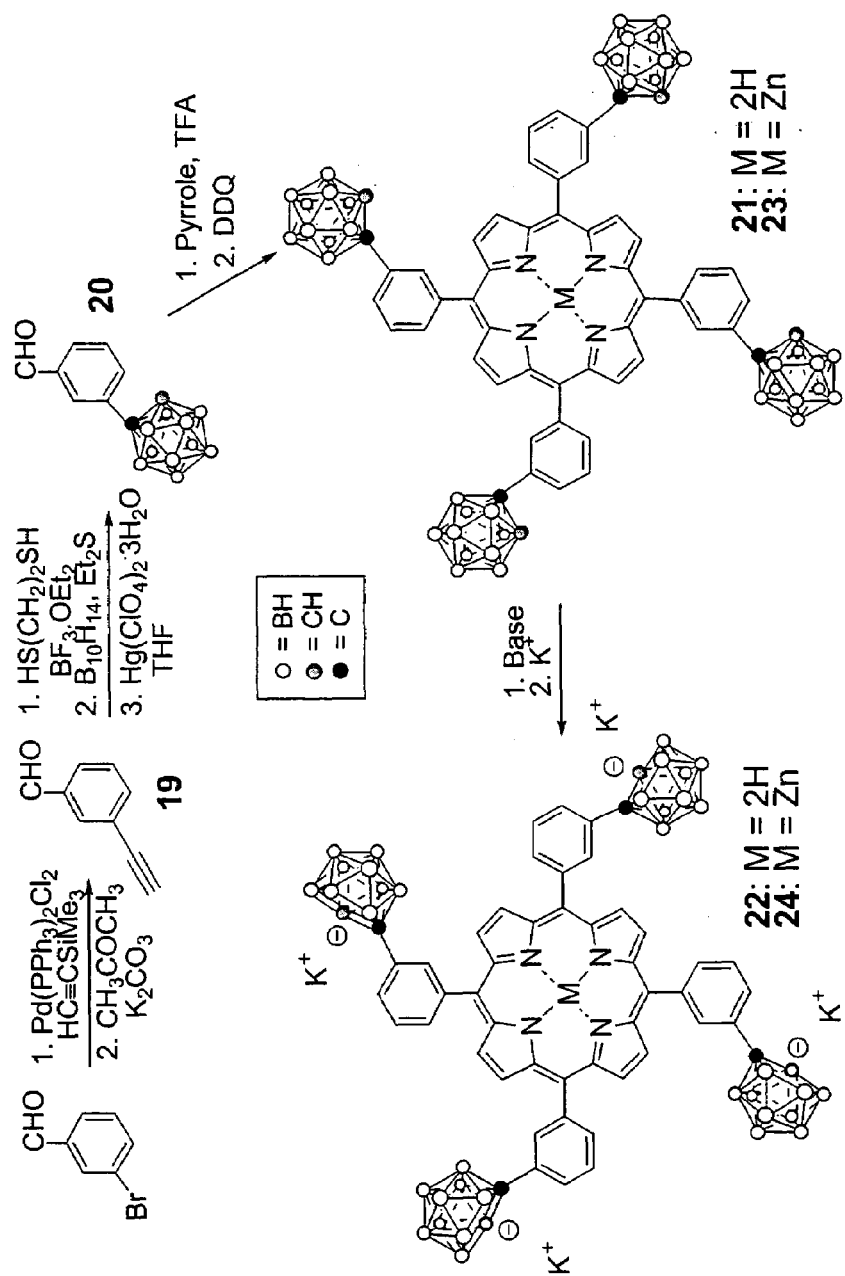
FIG. 4 (Scheme 4) depicts the synthesis of compounds 19-24.
Figure 5:
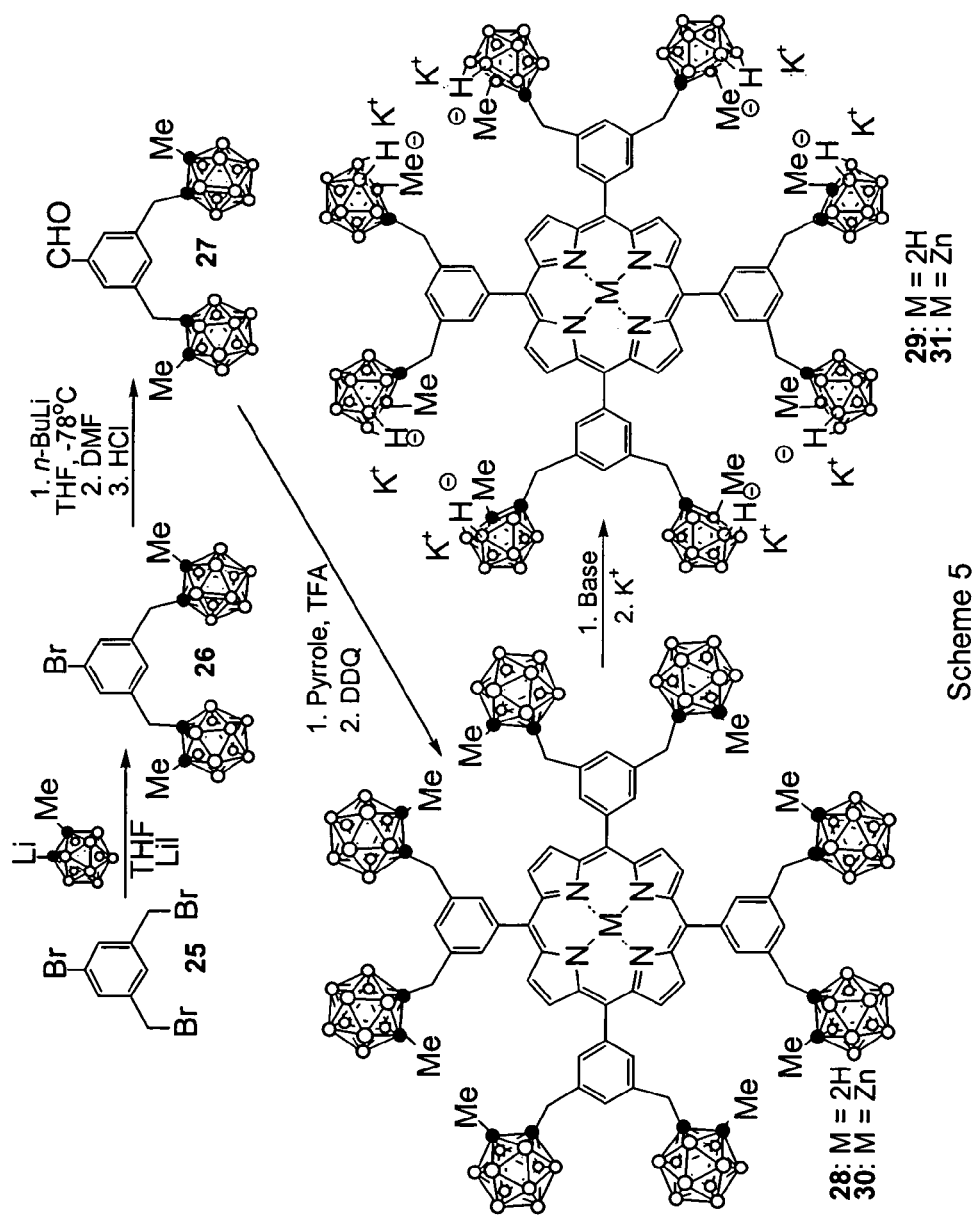
FIG. 5 (Scheme 5) depicts the synthesis of compounds 25-31.
Figure 6:
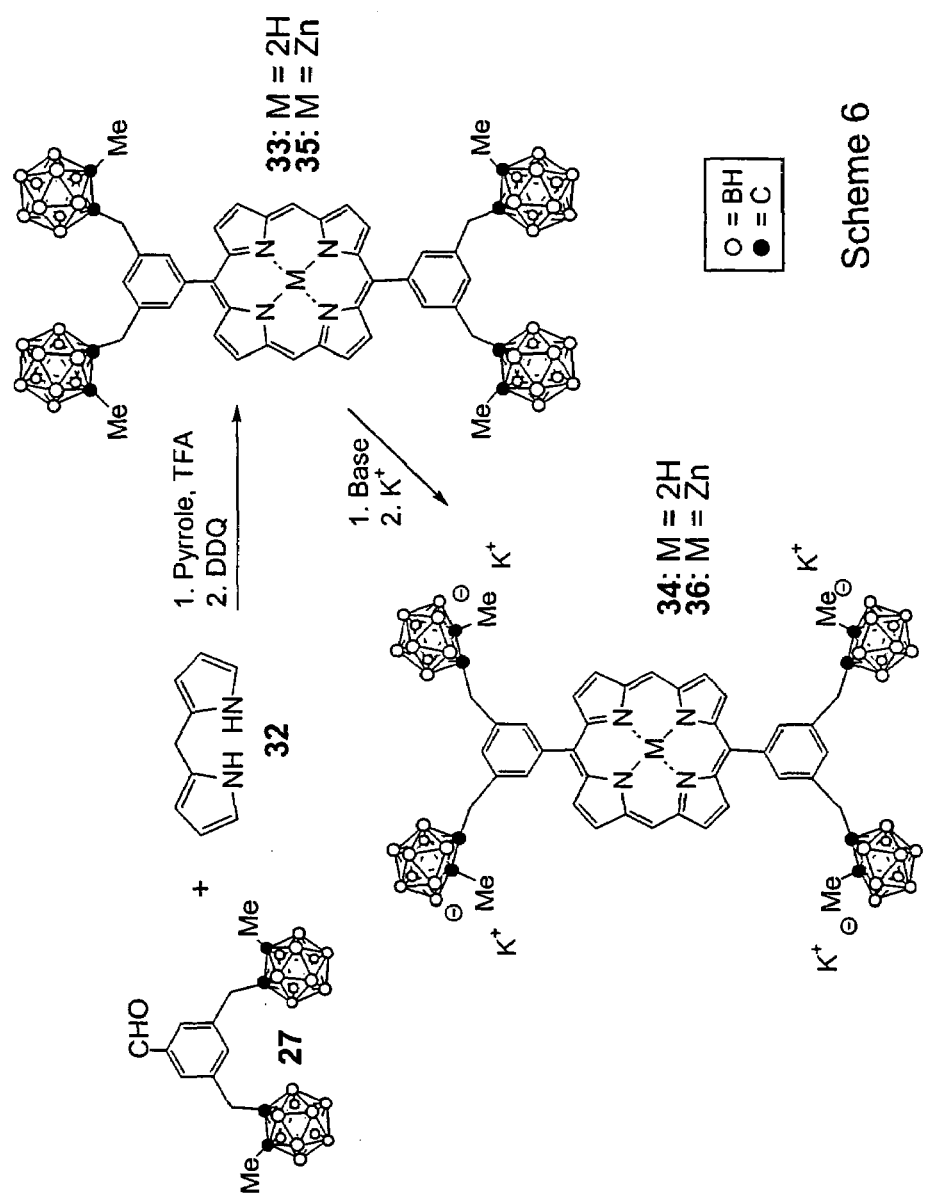
FIG. 6 (Scheme 6) depicts the synthesis of compounds 32-36.

This invention pertains to the use of certain porphyrin compounds containing carboranyl groups attached to the porphyrin group by a carbon-carbon linkage as chelating agents. As examples, these porphyrin compounds may correspond generally to formula I:

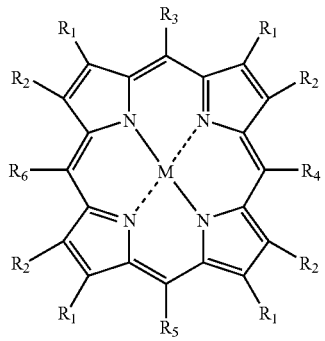

I where M is 2H or a metal ion, preferably a pentacoordinated or hexacoordinated metal ion; R1 and R2 are each independently hydrogen, alkyl or hydroxyalkyl; and R3 through R6 are each independently hydrogen, phenyl, or a substituted phenyl group.

Where one or more of R3 through R6 comprise a substituted phenyl group, that substituted phenyl group corresponds to general formula II:

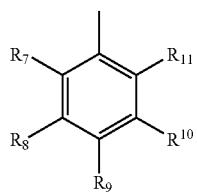

II where R7 through R11 are each independently hydrogen or a carboranyl group. The carboranyl group should be attached to the phenyl group by a carbon-carbon linkage (and not, for example, an ether linkage or an ester linkage). Typically, one or two of R7 through R11 are carboranyl groups.

At least one of R3 through R6 should be a substituted phenyl group of general formula II, having at least one carboranyl group attached by a carbon-carbon linkage. More preferably, at least two of R3 through R6 should be a substituted phenyl group of general formula II, each having at least one carboranyl group attached by a carbon-carbon linkage. Most preferably, all of R3 through R6 should be a substituted phenyl group of general formula II, each having at least one carboranyl group attached by a carbon-carbon linkage.

In a preferred embodiment, the compound has from 4 to 8 carboranyl substituents.

The carboranyl-containing porphyrin compounds used in this invention may be synthesized, for example, by the following general method. (Examples of specific syntheses are described in detail below.) A pyrrole or dipyrrole is reacted with a benzaldehyde using an acid catalyst, such as trifluoroacetic acid. The pyrrole or dipyrrole may be unsubstituted or substituted, for example with alkyl groups. The benzaldehyde has general formula III:

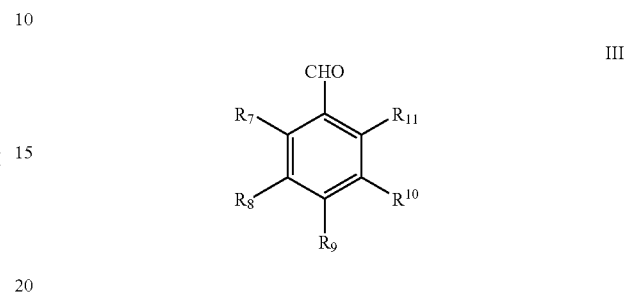

III where R7 through R11 are each independently hydrogen or a carboranyl group. The carboranyl group should be attached to the phenyl group by a carbon-carbon linkage (and not, for example, an ether linkage or an ester linkage). Typically, one or two of R7 through R11 are carboranyl groups. The next step is oxidation of the reaction mixture, for example, with tetrachloroquinone or dichlorodicyanobenzoquinone.

Optionally, the synthesis may include complexing the porphyrin compound with a penta- or hexa-coordinated metal ion, e.g., by treating the free base of the porphyrin compound with zinc chloride to form a Zn(II) complex.

FIGS. 1 through 6 depict, in a few steps, the total synthesis of various carboranylated phenylporphyrins. These meso-phenylporphyrin compounds contain carbon-carbon linkages between the carboranyl groups and the porphyrin ring for increased chemical stability. These compounds are soluble in aqueous solution.

In summary, the compounds preferred for use in the present invention contain carbon-carbon linkages between a porphyrin ring and 4-8 carboranyl groups, and are soluble in an aqueous environment.

EXAMPLES

Synthesis of Compound 1

[4-(1-methyl-o-carboranyl)methyl]bromobenzene (1)

A two-necked round bottom flask containing 1-methyl-o-carborane (5.00 g, 31.65 mmol) in dry DME (150 mL) was cooled to 0° C. under argon. n-BuLi (20.0 mL, 1.6 M in hexane) was added dropwise, and the resulting mixture was stirred at 0° C. for 30 minutes. A solution of 4-(bromomethyl)bromobenzene (7.91 g, 31.65 mmol) in dry DME (15 mL) was added dropwise. After stirring at 0° C. for 10 minutes, the final reaction mixture was warmed to room temperature and then refluxed for 12 hours under argon. The solvent was then removed under vacuum, and the crude solid obtained was purified by recrystallization from dichloromethane/methanol to give the title compound (7.80 g, 75.4% yield) as white crystals. MS (EI) m/e 327.1 (M$^+$); $^1$H-NMR (CDCl$_3$) δ ppm: 1.3-3.0 (br, 10H, BH), 2.15 (s, 3H, CH$_3$), 3.41 (s, 2H, CH$_2$), 7.06 (d, 2H, ArH, J=8.1 Hz), 7.48 (d, 2H, ArH, J=8.1 Hz).

Synthesis of Compound 2

[4-(1-Methyl-o-carboranyl)methyl]benzaldehyde (2)

A solution of compound 1 (4.00 g, 12.23 mmol) in THF (150 mL) under argon was cooled to −78° C. (acetone/dry ice bath). n-BuLi (7.6 mL, 1.6 M in hexane) was added dropwise while maintaining the temperature at −78° C. The reaction mixture was stirred for 30 minutes at −78° C., after which dry DMF (5.0 mL, 64.6 mmol) was slowly added. The final mixture was stirred at −78° C. for 15 minutes, and then warmed slowly to room temperature. A 2 N HCl solution (150 mL) was added, and the reaction mixture stirred for 2 h at room temperature. The solution was then reduced to a volume of 200 mL and extracted with dichloromethane (4×50 mL). The organic extracts were washed once with a saturated aqueous $NaHCO_3$ solution, and once with water, and were then dried over anhydrous $Na_2SO_4$. After removal of the solvent under vacuum, the oily residue was purified by column chromatography on silica gel (dichloromethane/petroleum ether 1:1), yielding the title compound (2.1 g, 62% yield) as a white solid. MS (EI) m/e 276.2 ($M^+$); $^1$H-NMR ($CDCl_3$) δ ppm: 1.5-3.0 (br, 10H, BH), 2.19 (s, 3H, $CH_3$), 3.54 (s, 2H, $CH_2$), 7.38 (d, 2H, ArH, J=8.0 Hz), 7.89 (d, 2H, ArH, J=8.0 Hz), 10.04 (s, 1H, CHO).

Synthesis of Compound 3 meso-tetra[4-(1-methyl-o-carboranyl)methylphenyl]porphyrin (3)

A solution of aldehyde 2 (1.16 g, 4.19 mmol) and freshly distilled pyrrole (0.30 mL, 4.32 mmol) in dry dichloromethane (420 mL) was purged with argon for 15 minutes. TFA (0.25 mL, 3.15 mmol) was added to the solution, and the final mixture was stirred at room temperature under argon for 20 hours (at which time the starting compound 2 had essentially disappeared completely, as assayed by TLC). After addition of p-chloranil (0.788 g, 3.14 mmol), the final reaction mixture was stirred at room temperature for 2 hours. The solution was concentrated under vacuum to 200 mL, then washed once with a saturated aqueous $NaHCO_3$ solution, and once with water, and were then dried over anhydrous $Na_2SO_4$. The residue after removal of the solvent under vacuum was purified by column chromatography (dichloromethane/petroleum ether 1:1), and the fastest-running porphyrin fraction was collected and recrystallized from dichloromethane/methanol, yielding 0.289 g (21% yield) of the title compound as purple crystals, m.p. >300° C.; MS (MALDI) m/e 1296.0 ($M^+$); $^1$H-NMR ($CDCl_3$) δ ppm: −2.80 (br, 2H, NH), 1.6-3.1 (br, 40H, BH), 2.34 (s, 12H, $CH_3$), 3.81 (s, 8H, $CH_2$), 7.59 (d, 8H, ArH, J=8.0 Hz), 8.20 (d, 8H, ArH, J=8.0 Hz), 8.85 (s, 8H, β-H). UV-Vis ($CHCl_3$) $\lambda_{max}$: 418 nm (ε467,700), 514 (16,867), 550 (8,132), 590 (5,470) (4,028).

Synthesis of Compound 4 meso-tetra[4-(1-methyl-nido-carboranyl)methylphenyl]porphyrin tetrapotassium salt (4)

Porphyrin 3 (0.050 g, 0.0386 mmol) was dissolved in a 3:1 mixture of pyridine and piperidine (4.0 mL), and then stirred at room temperature in the dark for 36 hours under argon. The solvent was completely removed under vacuum, the residue was re-dissolved in a 60% acetone aqueous solution, which was then passed slowly over a Dowex 50W2-100 resin in the potassium form. The porphyrin fraction was collected, dried under vacuum, re-dissolved in a 30% aqueous acetone solution, and again passed through the ion-exchange resin. After removal of the solvent under vacuum, the tetraanionic porphyrin was recrystallized from methanol/diethyl ether, yielding 0.051 g (94% yield) of the title compound, m.p. >300° C. $^1$H-NMR ($CD_3COCD_3$) δ ppm: −2.70 (s, 2H, NH), −2.45 to −1.90 (br, 4H, BH), 0.9-2.4 (br, 32H, BH), 1.59 (s, 12H, $CH_3$), 3.50 (s, 8H, $CH_2$), 7.81 (d, 8H, ArH, J=8.0 Hz), 8.08 (d, 8H, ArH, J=8.0 Hz), 8.90 (s, 8H, β-H). UV-Vis (acetone) $\lambda_{max}$: 420 nm (ε349,700), 516 (13,595), 554 (12,410), 594 (4,130), 650 (5,990).

Synthesis of Compound 5

Zn(II)-meso-tetra[4-(1-methyl-o-carborane)methylphenyl]porphyrin (5)

To a solution of porphyrin 3 (0.150 g) in dichloromethane (150 mL), THF (10 mL), and pyridine (0.5 mL) were added with $ZnCl_2.2H_2O$, and the final mixture was stirred at room temperature under argon overnight. The mixture was then washed once with water, dried over anhydrous $Na_2SO_4$, and the solvent evaporated under vacuum. The residue was purified by column chromatography (dichloromethane/petroleum ether 1:1.5), and the pink-colored fraction was collected and recrystallized from dichloromethane/methanol to give 0.135 g (92% yield) of the title compound as purple crystals, m.p. >300° C.; MS m/e 1358.6; $^1$H-NMR ($CDCl_3$) δ ppm: 1.6-3.0 (br, 40H, BH), 2.33 (s, 12H, $CH_3$), 3.80 (s, 8H, $CH_2$), 7.57 (br s, 8H, ArH), 8.19 (br s, 8H, ArH), 8.95 (br s, 8H, β-H). UV-Vis ($CHCl_3$) $\lambda_{max}$: 424 nm (ε577.000), 554 (20,102), 596 (6,380).

Synthesis of Compound 6

Zn(II)-meso-tetra[4-(1-methyl-nido-carboranyl)methylphenyl]porphyrin tetrapotassium salt (6)

The Zn(II) complex 5 (0.075 g, 0.055 mmol) was dissolved in a 3:1 mixture of pyridine and piperidine (4.0 mL), and stirred at room temperature in the dark for 36 hours under argon. The solvent was completely removed under vacuum, and the residue was re-dissolved in a 60% aqueous acetone solution and passed slowly through a Dowex 50W2-100 resin in potassium form. The porphyrin fraction was collected, dried under vacuum, re-dissolved in a 30% aqueous acetone solution, and again passed through the ion-exchange resin. After removal of the solvent under vacuum, the tetraanionic porphyrin was recrystallized from methanol/diethyl ether, yielding 0.078 g (96% yield) of the title compound, m.p. >300° C. $^1$H-NMR ($CD_3COCD_3$) δ ppm: −2.48 to −1.95 (br, 4H, BH), 0.9-2.4 (br, 32H, BH), 1.59 (s, 12H, $CH_3$), 3.50 (s, 8H, $CH_2$), 7.77 (d, 8H, ArH, J=8.0 Hz), 8.11 (d, 8H, ArH, J=8.0 Hz), 8.92 (s, 8H, β-H). UV-Vis (acetone) $\lambda_{max}$: 422 nm (ε479,000), 554 (13,870), 596 (6,595).

Synthesis of Compound 7

[3-(1-Methyl-o-carboranyl)methyl]bromobenzene (7)

A two-necked round bottom flask containing 1-methyl-o-carborane (3.00 g, 18.99 mmol) in dry THF (150 mL) was cooled to 0° C. under argon. n-BuLi (12.0 mL, 1.6 M in hexane) was added dropwise, and the resulting mixture was stirred at 0° C. and then cooled to −10° C. A solution of anhydrous LiI (0.350 g, 2.61 mmol) in THF (2.5 mL) was added, followed by a solution of 3-(bromomethyl)bromobenzene (5.00 g, 20.00 mmol) in THF (10 mL). After stirring at −10° C. for 15 minutes, the final reaction mixture was warmed to room temperature and stirred for 12 hours under argon. The reaction mixture was then washed with water (2×25 mL), extracted with diethyl ether (3×25 mL), and dried over $Na_2SO_4$. The solvent was then removed under vacuum, and the resulting crude solid was purified by column chromatography (silica gel, dichloromethane/petroleum ether 1:9) to give the title compound (4.25 g, 65.0% yield). $^1$H-NMR ($CDCl_3$) δ ppm: 1.3-3.1 (br, 10H, BH), 2.16 (s, 3H, $CH_3$), 3.42 (s, 2H, $CH_2$), 7.13 (d, 1H, ArH, J=7.8 Hz), 7.23 (t, 1H, ArH, J=7.8 Hz), 7.33 (s, 1H, ArH), 7.47 (d, 1H, ArH, J=7.8 Hz).

Synthesis of Compound 8

[3-(1-Methyl-o-carboranyl)methyl]benzaldehyde (8)

A solution of compound 7 (1.00 g, 3.06 mmol) in THF (25 mL) under argon was cooled to −78° C. (acetone/dry ice bath). n-BuLi (2.0 mL, 1.6 M in hexane) was added dropwise while maintaining the temperature at −78° C. The reaction mixture was stirred for 30 minutes at −78° C. before dry DMF (1.0 mL, 17.5 mmol) was slowly added. The final mixture was stirred at −78° C. for 15 minutes, and was then warmed slowly to room temperature. A 2 N HCl solution (25 mL) was added, and the reaction mixture was stirred for 2 h at room temperature. The solution was then reduced to a volume of 200 mL and extracted with dichloromethane (4×50 mL). The organic extracts were washed once with a saturated aqueous $NaHCO_3$ solution, and once with water, and were then dried over anhydrous $Na_2SO_4$. After removal of the solvent under vacuum, the oily residue was purified by column chromatography on silica gel (dichloromethane/petroleum ether 1:1), yielding the title compound (0.668 g, 79.1% yield) as a white solid. $^1$H-NMR ($CDCl_3$) δ ppm: 1.4-3.1 (br, 10H, BH), 2.19 (s, 3H, $CH_3$), 3.55 (s, 2H, $CH_2$), 7.48 (d, 1H, ArH, J=7.8 Hz), 7.56 (t, 1H, ArH, J=7.8 Hz), 7.70 (s, 1H, ArH), 7.85 (d, 1H, ArH, J=7.8 Hz), 10.04 (s, 1H, CHO).

Synthesis of Compound 9 meso-tetra[3-(1-methyl-o-carboranyl)methylphenyl]porphyrin (9)

A solution of aldehyde 8 (0.660 g, 2.39 mmol) and freshly distilled pyrrole (0.18 mL, 2.59 mmol) in dry dichloromethane (240 mL) was purged with argon for 45 minutes. TFA (0.15 mL, 1.89 mmol) was added to the solution, and the final mixture was stirred at room temperature under argon for 18 hours. After addition of p-chloranil (0.440 g, 1.77 mmol), the final reaction mixture was stirred at room temperature for 3 hours. The organic solution was washed once with a saturated aqueous $NaHCO_3$ solution, and once with water, and were then dried over anhydrous $Na_2SO_4$. The residue obtained after removal of the solvent under vacuum was purified by column chromatography (dichloromethane/petroleum ether 1:1), and the porphyrin fraction was collected and recrystallized from dichloromethane/methanol, yielding 0.252 g (33% yield) of the title compound as purple crystals, m.p. >300° C.; MS (MALDI) m/e 1296.0 ($M^+$); $^1$H-NMR ($CDCl_3$) δ ppm: −2.84 (br, 2H, NH), 1.5-3.0 (br, 40H, BH), 2.20 (s, 12H, $CH_3$), 3.74 (s, 8H, $CH_2$), 7.62 (d, 4H, ArH), 7.74 (d, 4H, ArH), 8.05 (d, 4H, ArH), 8.18 (d, 4H, ArH), 8.84 (s, 8H, β-H). UV-Vis ($CHCl_3$) $\lambda_{max}$: 419 nm, 516, 548, 590, 646.

Synthesis of Compound 10 meso-tetra[3-(1-methyl-nido-carboranyl)methylphenyl]porphyrin tetrapotassium salt (10)

Porphyrin 9 (0.049 g, 0.0378 mmol) was dissolved in a 3:1 mixture of pyridine and piperidine (4.0 mL), and stirred at room temperature in the dark for 36 hours under argon. The solvent was completely removed under vacuum, the residue re-dissolved in a 60% aqueous acetone solution, and was then passed slowly through a Dowex 50W2-100 resin in potassium form. The porphyrin fraction was collected, dried under vacuum, re-dissolved in a 30% aqueous acetone solution, and was again passed through the ion-exchange resin. After removal of the solvent under vacuum, the tetraanionic porphyrin was recrystallized from methanol/diethyl ether, yielding 0.050 g (94% yield) of the title compound, m.p. >300° C. UV-Vis (acetone) $\lambda_{max}$: 431 nm, 511, 546, 590, 647.

Synthesis of Compound 13

4-Ethynylbenzaldehyde (13)

To a solution of 4-bromobenzaldehyde (10.00 g, 54.08 mmol) and triphenylphosphine (0.500 g, 1.91 mmol) in anhydrous triethylamine (80 mL) under argon were added ethynyltrimethylsilane (6.00 g, 61.09 mmol) and palladium (II) acetate (0.100 g, 0.445 mmol). The final mixture was heated to reflux for 2 hours, and was then cooled to room temperature and filtered. The filtrate was concentrated under vacuum to a thick oil, which was purified by column chromatography (dichloromethane/petroleum ether 1:4) and recrystallized from cold cyclohexane to give 10.5 g (96.1% yield) of 4-(trimethylsilylethynyl)benzaldehyde [MS m/e 187.2 ($M^+$); $^1$H-NMR ($CDCl_3$) δ ppm: 0.27 (s, 9H, $SiMe_3$), 7.60 (d, 2H, ArH, J=8.1 Hz), 7.82 (d, 2H, ArH, J=8.1 Hz), 10.00 (s, 1H, CHO)]. This compound (8.00 g, 39.59 mmol) was treated with $K_2CO_3$ (0.500 g) in methanol (50 mL) at 25° C. for 2 hours under Argon. The solvent was removed under vacuum, and the residue was dissolved in dichloromethane (100 mL). This solution was washed once with a saturated aqueous $NaHCO_3$ solution, and once with water, was then dried over anhydrous $Na_2SO_4$, and the solvent was evaporated under vacuum. The yellow residue was purified by column chromatography using dichloromethane/petroleum ether 1:4, and then recrystallized from cold cyclohexane to give 4.40 g (85.5% yield) of the title compound; MS (EI) m/e 130.0; ($M^+$). $^1$H-NMR ($CDCl_3$) δ ppm: 3.30 (s, 1H, CH), 7.64 (d, 2H, ArH, J=8.1 Hz), 7.84 (d, 2H, ArH, J=8.1 Hz), 10.02 (s, 1H, CHO).

Synthesis of Compound 14

4-(o-carboranyl)benzaldehyde (14)

$BF_3.OEt_2$ (0.654 g, 4.62 mmol) was added under argon to a 0° C. solution of 4-ethynylbenzaldehyde (13) (6.00 g, 46.15 mmol) and 1.2-ethanedithiol (5.00 g, 53.09 mmol). The mixture was stirred at room temperature under argon for 15 minutes. The reaction mixture was then washed once with a 10% aqueous NaOH solution, and once with a saturated aqueous NaCl solution, before being dried over anhydrous Na$_2$SO$_4$. The solvent was then evaporated under vacuum. Purification of the resulting residue by column chromatography (dichloromethane/petroleum ether 1:4) gave p-ethynylbenzyl(1,3-dithiane) (7.5 g, 79% yield) as a yellow solid [MS (EI) m/e 206.0 (M$^+$); $^1$H-NMR (CDCl$_3$) d ppm: 3.07 (s, 1H, CH), 3.38 and 3.51 (m, 2H each, CH$_2$CH$_2$), 5.61 (s, 1H, SCH), 7.42 (d, 2H, ArH, J=8.1 Hz), 7.47 (d, 2H, ArH, J=8.1 Hz)]. Decaborane (3.00 g, 24.59 mmol), ethyl sulfide (5.00 g, 55.44 mmol), and dry toluene (50 mL) were combined in a Schlenk tube equipped with a stir bar. This solution was heated to 40° C. for 3 hours and to 60° C. for 2 hours, and was then allowed to cool to room temperature. To this mixture was added a solution of p-ethynylbenzyl(1,3-dithiane) (5.00 g, 24.26 mmol) in dry toluene (10 mL). The final reaction mixture was slowly warmed to 80° C., and was held at this temperature and stirred for 3 days. After then cooling to room temperature, the mixture was concentrated under vacuum and the resulting oil was dissolved in methanol (250 mL) and heated to reflux until liberation of hydrogen ceased (approximately 60 minutes). At room temperature a 50% aqueous HCl solution (2 to 3 mL) was cautiously added, and the mixture was again heated to reflux until hydrogen evolution was complete (approximately 30 minutes). After cooling to room temperature, the reaction mixture was diluted with ethanol, and excess ethyl sulfide was removed by ethanol-ethyl sulfide co-distillation. The remaining residue was concentrated under vacuum. To a solution of the resulting residue in benzene (100 mL) at 5° C. was added 100 mL of a cold 10% aqueous NaOH solution, and the final mixture was stirred vigorously for 15 minutes. The organic layer was separated, washed with water (3×25 mL), and dried over anhydrous Na$_2$SO$_4$. After evaporation of the solvent, the residue obtained was purified by column chromatography (dichloromethane/petroleum ether 1:4), yielding 5.25 g (66.8% yield) of p-(o-carboranyl) benzyl(1,3-dithiane) [MS (EI) m/e 324.1 (M$^+$); $^1$H-NMR (CDCl$_3$) δ ppm: 1.6-3.3 (br, 10H, BH), 3.36 and 3.47 (m, 2H each, CH$_2$CH$_2$), 3.91 (br s, 1H, o-carborane-CH), 5.56 (s, 1H, SCH), 7.40 (d, 2H, ArH, J=8.1 Hz), 7.46 (d, 2H, ArH, J=8.1 Hz)]. To a solution of this compound (5.00 g, 15.43 mmol) in 5% aqueous THF (25 mL) under argon was added dropwise a solution of HgClO$_4$ (12.50 g, 31.29 mmol) in THF (15 mL). The final mixture was stirred at room temperature for 15 minutes before being filtered, and the precipitate was washed 3 times with 25 mL diethyl ether. The filtrate was washed with a saturated aqueous Na$_2$CO$_3$ solution (3×25 mL) and with water (2×25 mL), before being dried over anhydrous Na$_2$SO$_4$. The residue remaining after evaporation of the solvent was purified by column chromatography (dichloromethane/petroleum ether 1:4) to give the title compound (3.27 g, 85.6% yield); MS (EI) m/e 248.2 (M$^+$); $^1$H-NMR (CDCl$_3$) δ ppm: 1.60-3.2 (br, 10H, BH), 4.03 (br s, 1H, o-carborane-CH), 7.65 (d, 2H, ArH, J=8.4 Hz), 7.86 (d, 2H, ArH, J=8.4 Hz), 10.04 (s, 1H, CHO).

Synthesis of Compound 15 meso-tetra[4-(o-carboranyl)phenyl]porphyrin (15)

A solution of aldehyde 14 (1.05 g, 4.23 mmol) and freshly distilled pyrrole (0.30 mL, 4.32 mmol) in dry dichloromethane (430 mL) was purged with argon for 30 minutes. TFA (0.20 mL, 2.52 mmol) was added to the solution, and the final mixture was stirred at room temperature under argon for 24 hours. After addition of p-chloranil (0.780 g, 3.14 mmol) the final reaction mixture was stirred at room temperature for 3 hours. The solution was concentrated under vacuum to 300 mL, then washed once with a saturated aqueous NaHCO$_3$ solution, and once with water before being dried over anhydrous Na$_2$SO$_4$. After evaporation of the solvent under vacuum, the resulting residue was purified by column chromatography (dichloromethane/petroleum ether 1:2), and the fastest-running porphyrin fraction was collected and recrystallized from dichloromethane/methanol, yielding 0.220 g (17.7% yield) of the title compound as purple crystals, m.p. >300° C.; MS (MALDI) m/e 1184.5 (M+1); $^1$H-NMR (CDCl$_3$) δ ppm: −2.89 (br, 2H, NH), 1.7-3.5 (br, 40H, BH), 4.28 (br s, 4H, o-carborane-CH), 7.89 (d, 8H, ArH, J=8.0 Hz), 8.17 (d, 8H, ArH, J=8.0 Hz), 8.78 (s, 8H, β-H). $^1$H-NMR (d-TFA/CDCl$_3$) δ ppm: −0.97 (br, 4H, NH), 1.8-3.4 (br, 40H, BH), 4.31 (br s, 4H, o-carborane-CH), 8.13 (d, 8H, J=8.0 Hz), 8.51 (d, 8H, J=8.0 Hz), 8.68 (s, 8H, β-H). UV-Vis (CHCl$_3$) λ$_{max}$: 418 nm (ε464,700), 514 (17,165), 550 (8,300), 590 (5,635), 646 (4,035).

Synthesis of Compound 16 meso-tetra[4-(nido-carboranyl)phenyl]porphyrin tetrapotassium salt (16)

Porphyrin 15 (0.0500 g, 0.0423 mmol) was dissolved in a 3:1 mixture of pyridine and piperidine (4.0 mL), and stirred at room temperature in the dark for 36 hours under argon. The solvent was completely removed under vacuum, the residue was re-dissolved in a 60% aqueous acetone solution, and was passed slowly through a Dowex 50W2-100 resin in potassium form. The porphyrin fraction was collected, dried under vacuum, re-dissolved in a 30% aqueous acetone solution, and again passed through the ion-exchange resin. After removal of the solvent under vacuum, the tetraanionic porphyrin was recrystallized from methanol/diethyl ether, yielding 0.0494 g (90.2% yield) of the title compound, m.p. >300° C. $^1$H-NMR (CD$_3$COCD$_3$) δ ppm: −2.78 (s, 2H, NH), −2.45 to −1.90 (br, 4H, BH), 0.8-2.4 (br, 32H, BH), 2.57 (br s, 4H, nido-carborane-CH), 7.66 (d, 8H, ArH, J=8.0 Hz), 7.97 (d, 8H, ArH, J=8.0 Hz), 8.87 (s, 8H, β-H). UV-Vis (acetone) λ$_{max}$: 420 nm (ε302,900), 516 (11,560), 554 (10,580), 594 (3,335), 650 (4,875).

Synthesis of Compound 17

Zn(II)-meso-tetra[4-(o-carboranyl)phenyl] porphyrin (17)

To a solution of porphyrin 15 (0.085 g, 0.072 mmol) in dichloromethane (50 mL), THF (4.0 mL), and pyridine (0.5 mL) was added ZnCl$_2$.2H$_2$O (0.30 g), and the final mixture was stirred at room temperature under argon overnight. The mixture was then washed once with water, dried over anhydrous Na$_2$SO$_4$, and the solvent was evaporated under vacuum. The residue was purified by column chromatography (dichloromethane/cyclohexane 1:2), and the pink-colored fraction was collected and recrystallized from dichloromethane/methanol to give 0.085 g (94.7% yield) of the title compound as purple crystals, m.p. >300° C.; MS (MALDI) m/e 1246.7 (M$^+$); $^1$H-NMR (CDCl$_3$) δ ppm: 1.6-3.6 (br, 40H, BH), 4.30 (br s, 4H, o-carborane-CH), 7.91 (br s, 8H, ArH), 8.17 (br s, 8H, ArH), 8.88 (br s, 8H, β-H). UV-Vis (CH$_2$Cl$_2$) λ$_{max}$: 424 nm (ε607,400), 554 (22,566), 594 (6,781).

Synthesis of Compound 18

Zn(II)-meso-tetra[4-(nido-carboranyl)phenyl]porphyrin tetrapotassium salt (18)

The Zn(II) complex 17 (0.0600 g, 0.0481 mmol) was dissolved in a 3:1 mixture of pyridine and piperidine (4.0 mL), and stirred at room temperature in the dark for 36 hours under argon. The solvent was completely removed under vacuum, and the residue was re-dissolved in a 60% aqueous acetone solution and passed slowly through a Dowex 50W2-100 resin in potassium form. The porphyrin fraction was collected, dried under vacuum, re-dissolved in a 30% aqueous acetone solution and again passed through the ion-exchange resin. After removal of the solvent under vacuum, the tetraanionic porphyrin was recrystallized from methanol/diethyl ether, yielding 0.0615 g (94.0% yield) of the title compound; $^1$H-NMR (CD$_3$COCD$_3$) δ ppm: -2.54 to -1.78 (br, 4H, BH), 0.6-2.2 (br, 32H, BH), 2.58 (brs, 4H, nido-carborane-CH), 7.64 (d, 8H, ArH, J=8.1 Hz), 7.95 (d, 8H, ArH, J=8.1 Hz), 8.88 (s, 8H β-H). UV-Vis (acetone) $\lambda_{max}$: 426 nm (ϵ432,000), 558 (14,380), 598 (9,513).

Synthesis of Compound 19

3-Ethynylbenzaldehyde (19)

To a solution of 3-bromobenzaldehyde (10.00 g, 54.08 mmol) and triphenylphosphine (0.500 g, 1.91 mmol) in anhydrous triethylamine (100 mL) under argon were added ethynyltrimethylsilane (6.00 g, 61.09 mmol) and palladium (II) acetate (0.100 g, 0.445 mmol). The final mixture was heated to reflux for 2 hours, and was then cooled to room temperature and filtered. The filtrate was concentrated under vacuum to a thick oil, which was purified by column chromatography (dichloromethane/petroleum ether 1:4) to give 8.52 g (78.0% yield) of 3-(trimethylsilylethynyl)benzaldehyde [$^1$H-NMR (CDCl$_3$) δ ppm: 0.26 (s, 9H, SiMe$_3$), 7.47 (t, 1H, ArH, J=7.5 Hz), 7.70 (d, 1H, ArH, J=7.5 Hz), 7.82 (d, 1H, ArH, J=7.5 Hz), 7.96 (s, 1H ArH), 9.98 (s, 1H, CHO)]. This compound (5.00 g, 24.74 mmol) was treated with K$_2$CO$_3$ (0.500 g) in methanol (50 mL) at 25° C. for 2 hours under argon. The solvent was removed under vacuum, and the residue was dissolved in dichloromethane (100 mL). This solution was washed once with a saturated aqueous NaHCO$_3$ solution, and once with water, before being dried over anhydrous Na$_2$SO$_4$ and the solvent evaporated under vacuum. The yellow residue was purified by column chromatography using dichloromethane/petroleum ether 1:4 for elution, and recrystallized from cyclohexane to give 2.80 g (87.1% yield) of the title compound; MS (EI) m/e 130.0; (M$^+$). $^1$H-NMR (CDCl$_3$) δ ppm: 3.20 (s, 1H, CH), 7.51 (t, 1H, ArH, J=7.8 Hz), 7.74 (d, 1H, ArH, J=7.8 Hz), 7.87 (d, 1H, ArH, J=7.8 Hz), 7.99 (s, 1H, ArH), 10.02 (s, 1H, CHO).

Synthesis of Compound 20

3-(o-carboranyl)benzaldehyde (20)

BF$_3$.OEt$_2$ (0.11 g, 0.77 mmol) was added at 0° C. under argon to a solution of 3-ethynylbenzaldehyde (19) (1.00 g, 7.69 mmol) and 1,2-ethanedithiol (0.73 g, 7.75 mmol). This mixture was stirred at room temperature under argon for 15 minutes. The reaction mixture was then washed once with a 10% aqueous NaOH solution, once with an aqueous saturated NaHCO$_3$ solution, and once with water before it was dried over anhydrous Na$_2$SO$_4$ and the solvent was evaporated under vacuum. Purification of the resulting residue by column chromatography (dichloromethane/petroleum ether 1:4) gave 1.28 g (80.7% yield) of m-ethynylbenzyl(1,3-dithiane) [MS (EI) m/e 206.0 (M$^+$); $^1$H-NMR (CDCl$_3$) d ppm: 3.07 (s, 1H, CH), 3.37 and 3.50 (m, 2H each, CH$_2$CH$_2$), 5.59 (s, 1H, SCH), 7.27 (t, 1H, ArH, J=7.8 Hz), 7.38 (d, 1H, ArH, J=7.8 Hz), 7.50 (d, 1H, ArH, J=7.8 Hz), 7.66 (s, 1H, ArH)]. Decaborane (0.0500 g, 4.10 mmol), ethyl sulfide (0.750 g, 8.32 mmol) and dry toluene (25 mL) were combined in a Schlenk tube equipped with a stir bar. This solution was heated to 40° C. for 3 hours and to 60° C. for 2 hours, and was then allowed to cool to room temperature. To this mixture was added a solution of m-ethynylbenzyl (1,3-dithiane) (0.800 g, 3.88 mmol) in dry toluene (5 mL), and the final reaction mixture was slowly warmed to 80° C., and was stirred at this temperature for 3 days. After cooling to room temperature, the mixture was concentrated under vacuum and the resulting oil was dissolved in methanol (100 mL) and heated to reflux until liberation of hydrogen subsisted (approximately 60 minutes). At room temperature a 50% aqueous HCl solution (1.0 mL) was cautiously added, and the mixture was again heated to reflux until hydrogen evolution was complete (approximately 30 minutes). After cooling to room temperature, the reaction mixture was diluted with ethanol, and the excess ethyl sulfide was removed by ethanol-ethyl sulfide co-distillation. The remaining residue was concentrated under vacuum. To a solution of the resulting residue in benzene (50 mL) at 5° C. was added 100 mL of a cold 10% aqueous NaOH solution, and the final mixture was stirred vigorously for 15 minutes. The organic layer was separated, washed with water (3×15 mL) and dried over anhydrous Na$_2$SO$_4$. After evaporation of the solvent, the resulting residue was purified by column chromatography (dichloromethane/petroleum ether 1:4), yielding 0.905 g (72.0% yield) of m-(o-carboranyl)benzyl (1,3-dithiane) [$^1$H-NMR (CDCl$_3$) δ ppm: 1.40-3.20 (br, 10H, BH), 3.39 and 3.49 (m, 2H each, CH$_2$CH$_2$), 3.97 (br s, 1H, o-carborane-CH), 5.58 (s, 1H, SCH), 7.28 (t, 1H, ArH, J=7.8 Hz), 7.39 (d, 1H, ArH, J=7.8 Hz), 7.55 (d, 1H, ArH, J=7.8 Hz), 7.63 (s, 1H, ArH)]. To a solution of the latter compound (1.00 g, 3.09 mmol) in 5% aqueous THF (10 mL) under argon was added dropwise a solution of HgClO$_4$ (2.50 g, 6.26 mmol) in THF (5.0 mL). The final mixture was stirred at room temperature for 15 minutes before being filtered, and the precipitate was washed with 25 mL of diethyl ether. The filtrate was then washed with a saturated aqueous Na$_2$CO$_3$ solution (3×10 mL) and with water (2×10 mL), before being dried over anhydrous Na$_2$SO$_4$. The residue remaining after evaporation of the solvent was purified by column chromatography (dichloromethane/petroleum ether 1:4) to give the title compound (0.677 g, 88.5% yield); $^1$H-NMR (CDCl$_3$) δ ppm: 1.5-3.3 (br, 10H, BH), 4.04 (br s, 1H, o-carborane-CH), 7.56 (t, 1H, ArH, J=7.8 Hz), 7.79 (d, 1H, ArH, J=7.8 Hz), 7.91 (d, 1H, ArH, J=7.8 Hz), 7.96 (s, 1H, ArH), 10.02 (s, 1H, CHO).

Synthesis of Compound 21 meso-tetra[3-(o-carboranyl)phenyl]porphyrin (21)

A solution of aldehyde 20 (0.702 g, 2.83 mmol) and freshly distilled pyrrole (0.200 mL, 2.88 mmol) in dry dichloromethane (285 mL) was purged with argon for 30 minutes. TFA (0.100 mL, 1.26 mmol) was added to the solution, and the final mixture was stirred at room temperature under argon for 18 hours. After addition of p-chloranil (0.522 g, 2.10 mmol) the final reaction mixture was stirred at room temperature for 3 hours. The solution was concentrated under vacuum to 200 mL, then washed once with water, once with a saturated aqueous NaHCO$_3$ solution, and once again with water before being dried under anhydrous Na$_2$SO$_4$. After evaporation of the solvent under vacuum, the resulting residue was purified by column chromatography (dichloromethane/petroleum ether 1:2) and the fastest-running porphyrin fraction was collected and recrystallized from dichloromethane/methanol, yielding 0.140 g (16.7% yield) of the title compound as purple crystals; MS (MALDI) m/e 1184. $^1$H-NMR (CDCl$_3$) δ ppm: −2.88 (br, 2H, NH), 1.6-3.5 (br, 40H, BH), 4.19 (br s, 4H, o-carborane-CH), 7.78 (m, 4H, ArH), 7.94 (m, 4H, ArH), 8.27 (m, 4H, ArH), 8.33 (m, 4H, ArH), 8.80 (s, 8H, β-H).

Synthesis of Compound 22 meso-tetra[3-(nido-carboranyl)phenyl]porphyrin tetrapotassium salt (22)

Porphyrin 21 (0.010 g, 0.008 mmol) was dissolved in a 3:1 mixture of pyridine and piperidine (4.0 mL), and the mixture was stirred at room temperature in the dark for 36 hours under argon. The solvent was completely removed under vacuum, and the residue was re-dissolved in a 60% aqueous acetone solution and then passed slowly through a Dowex 50W2-100 resin in potassium form. The porphyrin fraction was collected, dried under vacuum, re-dissolved in a 30% aqueous acetone solution and again passed through the ion-exchange resin. After removal of the solvent under vacuum, the tetraanionic porphyrin was recrystallized from methanol/diethyl ether, yielding 0.0108 g (98.1% yield) of the title compound, m.p. >300° C. $^1$H-NMR (CD$_3$COCD$_3$) δ ppm −2.70 (s, 2H, NH), −2.40 to −1.90 (br, 4H, BH), 0.8-2.3 (br, 32H, BH), 2.48 (br s, 4H, nido-carborane-CH), 7.49 (m, 4H, ArH), 7.65 (m, 4H, ArH), 7.84 (m, 4H, ArH), 8.15 (m, 4H, ArH), 8.88 (s, 8H, β-H). UV-Vis (acetone) $\lambda_{max}$: 416 nm (ε326,300), 512 (14,300), 547 (8,000), 590 (4,300), 646 (4,300).

Synthesis of Compound 25

Bis-(3,5-bromomethyl)bromobenzene (25)

To a refluxing solution of 3,5-dimethylbromobenzene (4.63 g) in dry CCl$_4$ (300 mL) under argon were added NBS (9.79 g) and benzoyl peroxide (0.80 g) in portions over a one hour period. The final reaction mixture was refluxed with stirring under argon for 16 hours. After cooling to room temperature, the reaction mixture was filtered, and the filtrate was washed once with a saturated aqueous NaHCO$_3$ solution and once with water. The organic solution was dried over anhydrous Na$_2$SO$_4$, and the solvent was evaporated under vacuum. The resulting residue was purified by column chromatography using dichloromethane/petroleum ether 1:9, and the main product was collected and recrystallized from n-hexane, yielding 2.83 g (33% yield) of the title compound; $^1$H-NMR (CDCl$_3$) δ ppm: 4.40 (s, 2H, CH$_2$), 7.34 (s, 1H), 7.47 (s, 2H).

Synthesis of Compound 26

Bis[3,5-(1-methyl-o-carboranyl)methyl]bromobenzene (26)

n-BuLi (5.2 mL, 1.6 M in hexane) was added dropwise to a solution of methyl-o-carborane (1.39 g, 8.80 mmol) in dry THF (80 mL), at a temperature between −5° and 0° C. under argon. The mixture was stirred at this temperature range for 90 minutes, and then cooled to −15° to −20° C. (ice/salt bath). A solution of LiI (0.166 g, 1.27 mmol) in dry THF (15 mL) and compound 25 (1.372 g, 4.00 mmol) was added, and the final reaction mixture was allowed to warm to room temperature and was stirred for 16 hours. After the reaction was quenched with water, the resulting mixture was extracted with diethyl ether. The organic extracts were washed once with water and once with brine, were dried over anhydrous Na$_2$SO$_4$, and the solvent was removed under vacuum. The crude product was purified by column chromatography using dichloromethane/petroleum ether 2:8 for elution, and the main product was collected and recrystallized from n-hexane to give 1.26 g (63% yield) of the title compound; MS m/e 497.3; $^1$H-NMR (CDCl$_3$) δ ppm: 1.4-3.0 (br, 20H, BH), 2.17 (s, 6H, CH$_3$), 3.43 (s, 4H, CH$_2$), 6.96 (s, 1H), 7.31 (s, 2H).

Synthesis of Compound 27

Bis[3,5-(1-methyl-o-carboranyl)methyl]benzaldehyde (27)

A solution of compound 26 (0.994 g) in THF (20 mL) under argon was cooled to −78° C. n-BuLi (1.4 mL, 1.6 M in hexane) was added dropwise via syringe. After the reaction mixture was stirred for 30 minutes at −78° C., dry DMF (0.77 mL) was slowly added. The resulting yellow mixture was stirred at −78° C. for 30 minutes, and was then warmed to 0° C. and stirred at this temperature for one hour. A 5% aqueous HCl solution was added until the pH of the reaction mixture was between 2 and 3, and the final mixture was then stirred at room temperature. The aqueous layer was extracted 4 times with diethyl ether, the organic fraction was dried over anhydrous MgSO$_4$, and the solvent was evaporated under vacuum. Purification by column chromatography (dichloromethane/petroleum ether 2:3), afforded the title compound (0.632 g) in 70.9% yield; MS m/e 446.4; $^1$H-NMR (CDCl$_3$) δ ppm: 1.5-3.0 (br, 20H, BH), 2.20 (s, 6H, CH$_3$), 3.55 (s, 4H, CH$_2$), 7.30 (d, 1H, J=1.6 Hz), 7.67 (d, 2H, J=1.6 Hz), 10.03 (s, 1H, CHO).

Synthesis of Compound 28 meso-tetra[bis-3,5-(1-methyl-o-carboranyl)methylphenyl]porphyrin (28)

A solution of aldehyde 27 (0.243 g, 0.54 mmol) and freshly distilled pyrrole (0.050 mL g, 0.72 mmol) in dry dichloromethane (55 mL) was purged with argon for 15 minutes. TFA was added, and the final solution was stirred at room temperature overnight (until the starting aldehyde had completely disappeared, and 2 new spots had formed as assayed by TLC). After oxidation with p-chloranil (0.102 g, 0.41 mmol) for 6 hours at room temperature, the final reaction mixture was washed once with a saturated aqueous NaHCO$_3$ solution and once with water before being dried over anhydrous Na$_2$SO$_4$. The residue obtained after removal of the solvent was purified by column chromatography using dichloromethane/petroleum ether 1:2 for elution. The porphyrin fraction obtained was recrystallized from dichloromethane/methanol, to give 0.30 g (12% yield) of the title compound; MS m/e 1977.3 $^1$H-NMR (d-TFA/CDCl$_3$) δ ppm: −0.80 (br, NH), 1.5-3.1 (br, 80H, BH), 2.31 (s, 24H, CH$_3$), 3.91 (s, 16H, CH$_2$), 7.72 (s, 4H), 8.33 (s, 8H), 8.74 (s, 8H, β-H).

Compounds 29-31

The synthesis of compounds 29-31 is depicted in Scheme 5.

Synthesis of Compound 33

5,15-bis[bis-3,5-(1-methyl-o-carboranyl)methylphenyl]porphyrin (33)

A solution of aldehyde 27 (0.446 g) and dipyrromethane 32 (0.146 g) in dry dichloromethane (100 mL) was purged with argon for 15 minutes and cooled to 0° C. TFA was added to the solution, and the final mixture was stirred at 0° C. for 2 hours and then at room temperature overnight. After oxidation with p-chloranil (0.277 g, 1.13 mmol) for 6 hours at room temperature, the final reaction mixture was washed once with a saturated aqueous NaHCO$_3$ solution, once with water, and once with brine before being dried over anhydrous MgSO$_4$. The residue obtained after removal of the solvent was purified by column chromatography (alumina) using dichloromethane for elution. The porphyrin fraction obtained was recrystallized from acetone to give 33.6% yield (0.192 g) of the title compound; MS m/e 1144.0; $^1$H-NMR (d-TFA/CDCl$_3$) δ ppm: −1.92 (br, NH), 1.4-3.2 (br, 40H, BH), 2.30 (s, 12H, CH$_3$), 3.89 (s, 8H, CH$_2$), 7.71 (s, 2H), 8.34 (s, 4H), 9.03 (d, 4H, β-H, J=4.5 Hz), 9.61 (d, 4H, β-H, J=4.5 Hz), 10.98 (s, 2H, meso-H).

Synthesis of Compound 34

5,15-bis[bis-3,5-(1-methyl-nido-carboranyl)methylphenyl]porphyrin tetrapotassium salt (34)

Porphyrin 33 (0.100 g) was dissolved in a 3:1 mixture of pyridine and piperidine (4.0 mL), and stirred at room temperature in the dark for 36 hours under argon. The solvent was completely removed under vacuum, the residue was re-dissolved in a 60% aqueous acetone solution and passed slowly through a Dowex 50W2-100 resin in potassium form. The porphyrin fraction was collected, dried under vacuum, re-dissolved in a 30% acetone aqueous solution and again passed through the ion-exchange resin. After removal of the solvent under vacuum, the tetraanionic porphyrin was recrystallized from methanol/diethyl ether, yielding 0.102 g (92.8% yield) of the title compound. $^1$H-NMR (CD$_3$COCD$_3$) δ ppm: −2.84 (s, 2H, NH), −2.45 to −1.85 (br, 4H, BH), 0.9-2.4 (br, 32H, BH), 1.66 (s, 12H, CH$_3$), 3.52 (s, 8H, CH$_2$), 7.67 (s, 1H, ArH), 7.74 (s, 1H, ArH), 8.37 (s, 4H, ArH), 9.53 (dd, 4H, β-H), 9.61 (dd, 4H, β-H), 10.58 (s, 2H, meso-H). UV-Vis (acetone) λ$_{max}$: 406 nm (ε312,600), 502 (13,400), 536 (7,800), 576 (6,100), 630 (3,100).

Synthesis of Compound 35

Zn(II)-5,15-bis[bis-3,5-(1-methyl-o-carboranyl)methylphenyl]porphyrin (35)

To a solution of porphyrin 33 (0.065 g, 0.057 mmol) in dichloromethane (100 mL) and THF (10 mL) was added ZnCl$_2$.2H$_2$O (0.031 g, 0.288 mmol), and the final mixture was stirred at room temperature under argon overnight. The mixture was then washed once with water, dried over anhydrous Na$_2$SO$_4$, and the solvent was evaporated under vacuum. The residue was purified by column chromatography (dichloromethane/cyclohexane 2:1), and the pink-colored fraction was collected and recrystallized from dichloromethane/methanol to give 0.061 g (89% yield) of the title compound. $^1$H-NMR (CDCl$_3$) δ ppm: 1.4-3.0 (br, 40H, BH), 2.11 (s, 12H, CH$_3$), 3.64 (s, 8H, CH$_2$), 7.33 (s, 2H, ArH), 7.98 (s, 4H, ArH), 8.98 (d, 4H, β-H, J=4.5 Hz), 9.41 (d, 4H, β-H, J=4.5 Hz), 10.25 (s, 2H, meso-H).

Synthesis of Compound 36

Zn(II)-5,15-bis[bis-3,5-(1-methyl-nido-carboranyl) methylphenyl]porphyrin tetrapotassium salt (36)

The Zn(II) complex 35 (0.050 g) was dissolved in a 3:1 mixture of pyridine and piperidine (4.0 mL), and was stirred at room temperature in the dark for 36 hours under argon. The solvent was completely removed under vacuum, the residue was re-dissolved in a 60% aqueous acetone solution, and was passed slowly through a Dowex 50W2-100 resin in potassium form. The porphyrin fraction was collected, dried under vacuum, re-dissolved in a 30% aqueous acetone solution and again passed through the ion-exchange resin. After removal of the solvent under vacuum, the tetraanionic porphyrin was recrystallized from methanol/diethyl ether, yielding 0.052 g (94.8% yield) of the title compound; $^1$H-NMR (CD$_3$COCD$_3$) δ ppm: −2.45 to −1.85 (br, 4H, BH), 0.9-2.4 (br, 32H, BH), 1.65 (s, 12H, CH$_3$), 3.50 (s, 8H, CH$_2$), 7.66 (s, 1H, ArH), 7.73 (s, 1H, ArH), 8.28 (s, 4H, ArH), 9.41 (dd, 4H, β-H), 9.47 (dd, 4H, β-H), 10.33 (s, 2H, meso-H). UV-Vis (acetone) λ$_{max}$: 412 nm (ε263,100), 496 (1,400), 542 (9,900), 580 (1,070), MS (MALDI) m/e 1319.4.

In Vitro Analysis of Boronated Porphyrins
Biological Studies

In vitro studies using rat 9 L gliosarcoma cells, mouse B16 melanoma cells, hamster V79 fibroblast cells, and human U-373MG glioblastoma cells have been conducted. We found that all compounds studied had very low dark cytotoxicities, were readily taken up and retained by cells, and were localized in specific cell organelles, primarily those in close proximity to the cell nucleus.

Our biological studies to date have indicated that these compounds have very low in vivo toxicities. So far we have determined maximum tolerated doses for compounds 4, 6, 16, 31, and 33 using healthy female Balb/c mice. For all compounds tested, we found that the maximum tolerated dose exceeded 300 mg per kg of body weight.

Cytotoxicity/Phototoxicity Assays

Human glioblastoma U373 MG, hamster V79 fibroblast, and mouse melanoma B16 cells were obtained from the American Type Culture Collection. Rat gliosarcoma cells were kindly provided by the University of California at San Francisco Brain Tumor Research Group. All cells were maintained in log phase monolayer cultures with RPMI 1640 supplemented with 10% fetal bovine serum and 2 mM glutamine.

Cells were seeded in 96-well culture plates, and were allowed to settle and attach for 24-48 hours. Triplicate wells were then exposed to twofold serial dilutions of test compounds at concentrations up to 250 µM. Compounds 4, 6, 10, and 12 in crystalline form were carefully weighed and dissolved in 100% DMSO to prepare stock solutions. Subsequent dilutions were performed directly in the culture medium just before the medium was administered to cells. After short-term (2 hour) or long-term (24 hour) exposure, cells were washed, and the wells were refilled with fresh culture medium. For dark toxicity trials, cells were allowed to proliferate for an additional 48-72 hours. For phototoxicity trials, washed cells were irradiated for 10 minutes with broad spectrum (600-700 nm) red light, and were then returned to an incubator for 48-72 hours.

Exposure to one of the compounds for 2 hours, followed by washing out the compound, did not inhibit proliferation of any of the three cell types. Exposure for 24 hours was inhibitory only at the higher concentrations (IC$_{50}$≧150 µM) for 9L and U-373 MG cells, but B16 viability was unaffected. Whereas the metal-free porphyrins 4 and 10 displayed nearly identical IC$_{50}$ values (∼150 µM) in the affected cells, their Zn(II) complexes were about 20% less toxic (IC$_{50}$∼180-185 µM).

We have also determined the cytotoxicity of porphyrins 4, 16, 18, and 31 in V79 hamster fibroblast cells using a clonogenic assay. For each of these porphyrins, we found $CS_{50} > 300$ μM, and we observed no toxicity (i.e., no effect on colony survival) at concentrations up to 200 μM.

In summary, these results showed that the nido-carboranyl compounds of the present invention display low dark toxicity.

Binding Experiments

Figure 7:
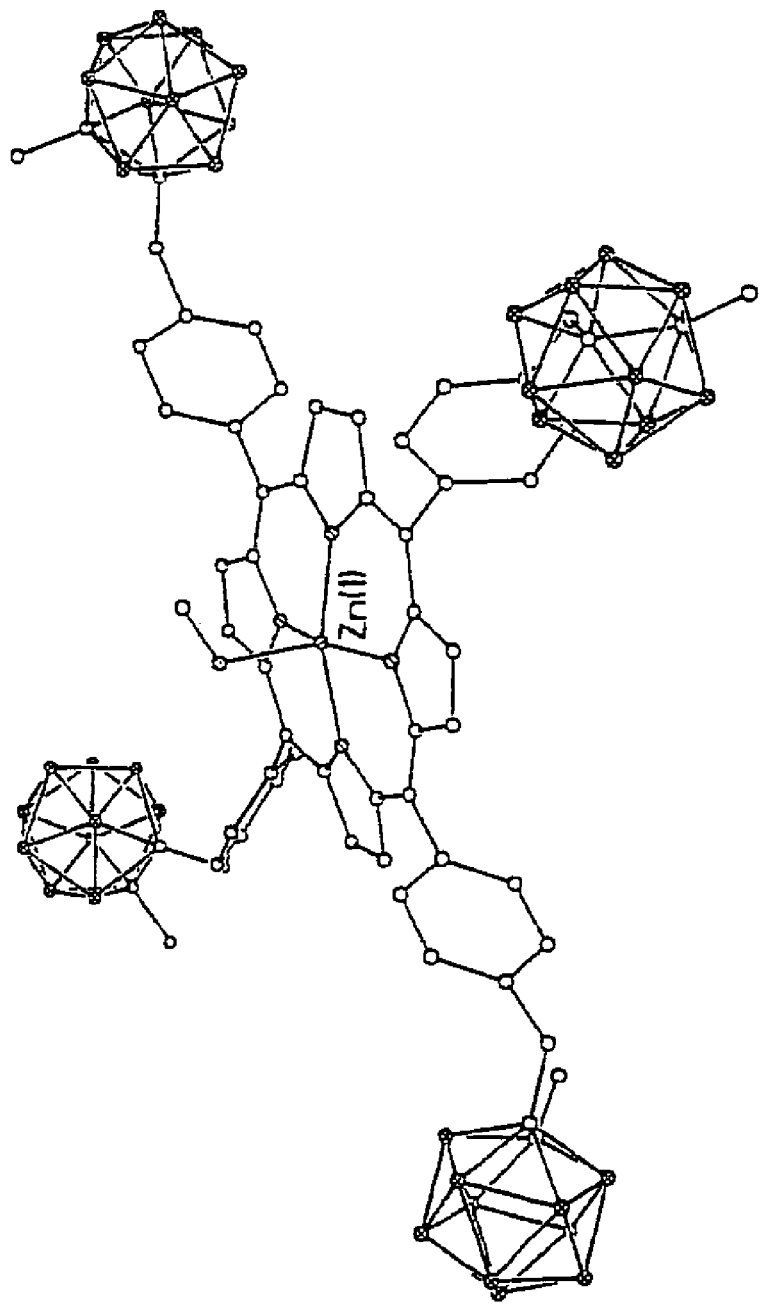
FIG. 7 depicts the structure inferred from X-ray data for compound 5 binding a methanol molecule axially.
Figure 8:
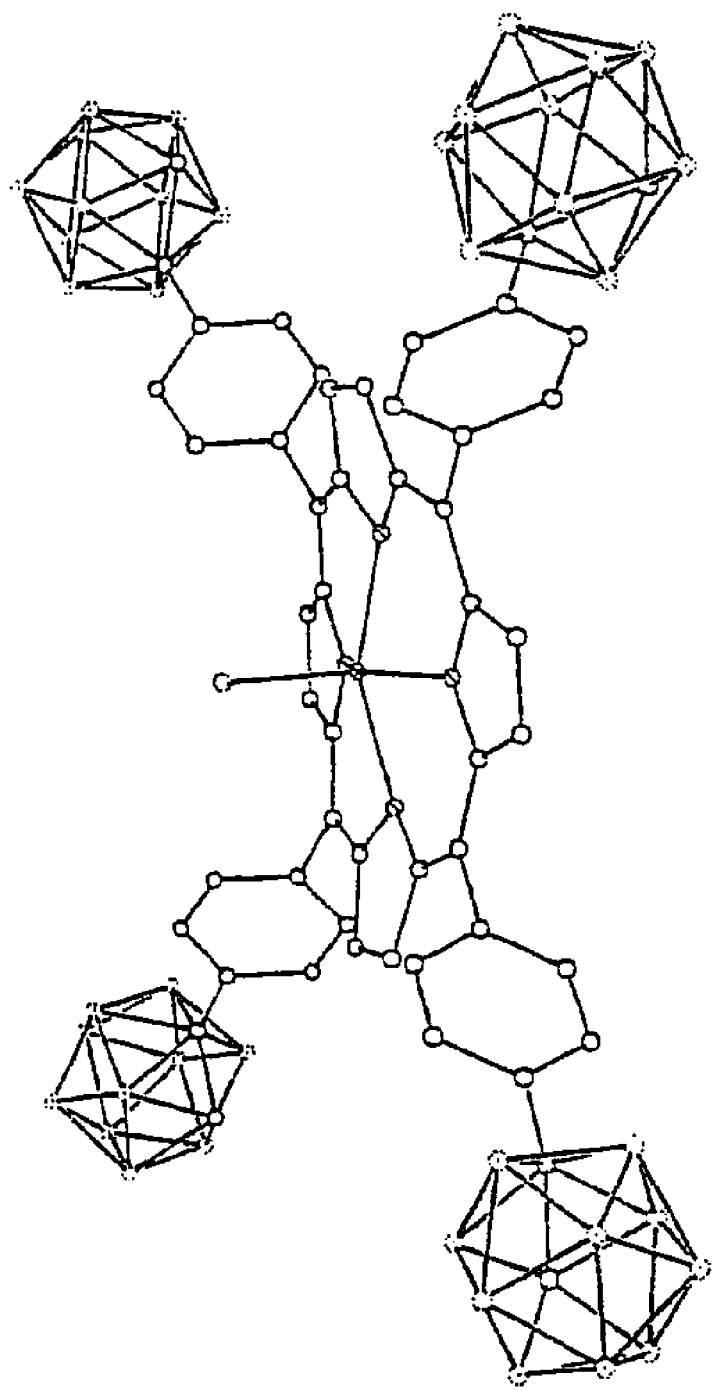
FIG. 8 depicts the structure inferred from X-ray data for compound 17 binding a water molecule axially.
Figure 9:
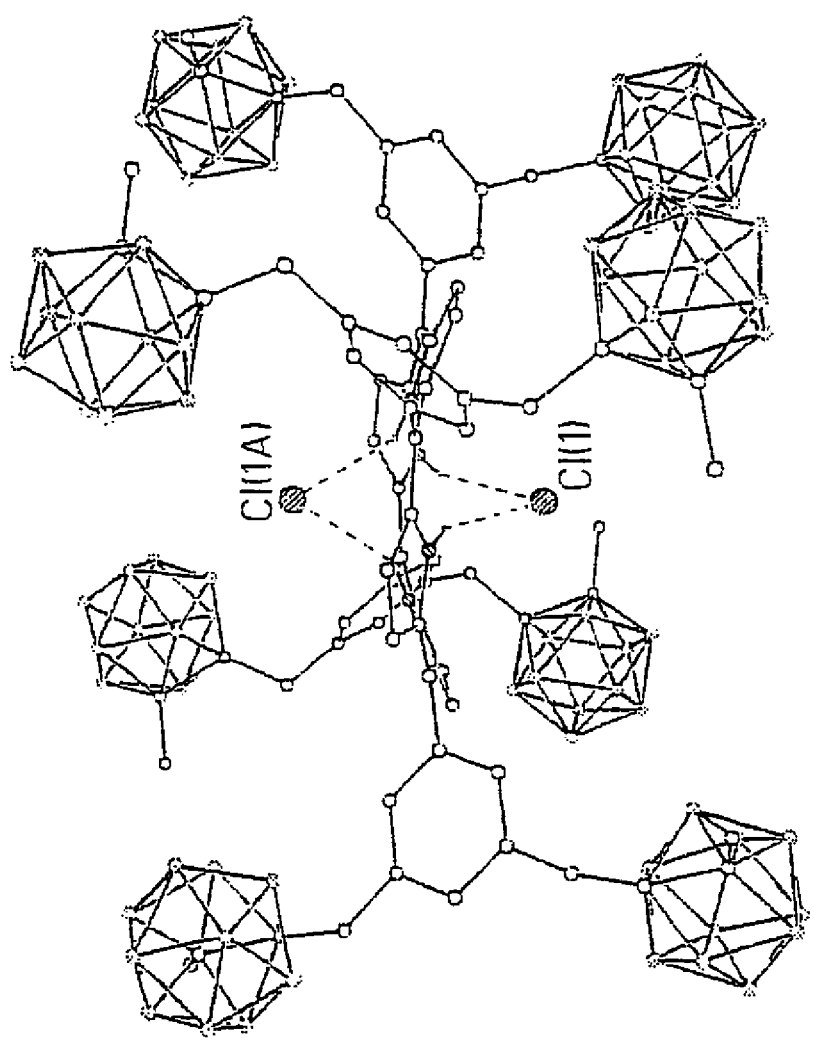
FIG. 9 depicts the structure inferred from X-ray data for compound 28 binding two chloride ions axially.
Figure 10:
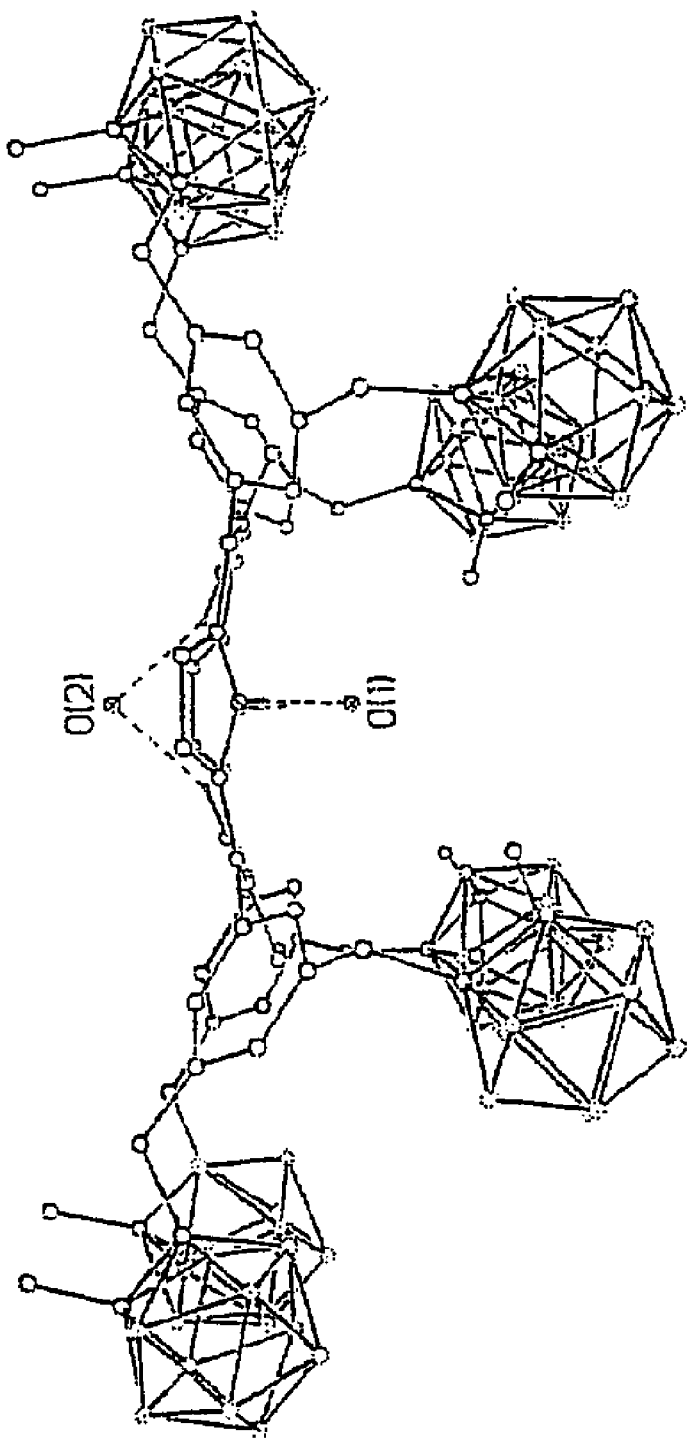
FIG. 10 depicts the structure inferred from X-ray data for compound 28 binding oxygen atoms from two picrate ions axially.
Figure 11:
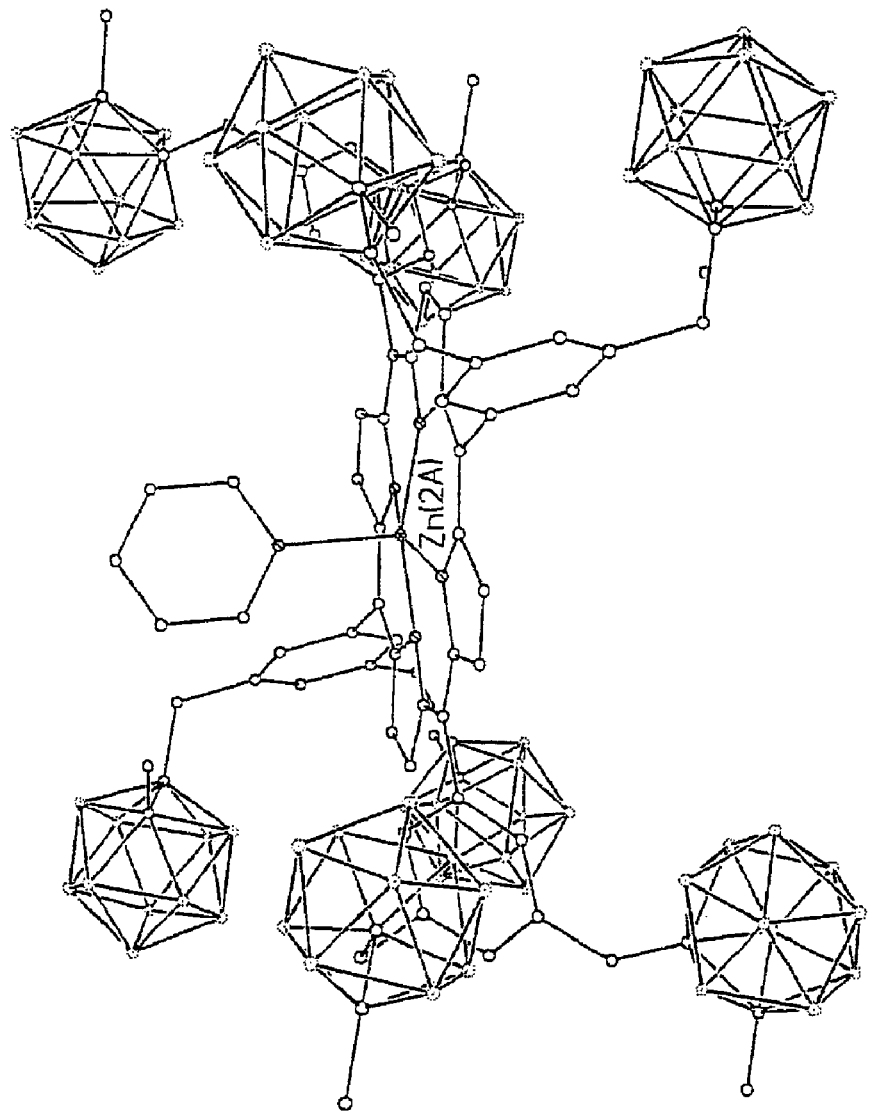
FIG. 11 depicts the structure inferred from X-ray data for compound 30 binding a pyridine molecule axially.
Figure 12:
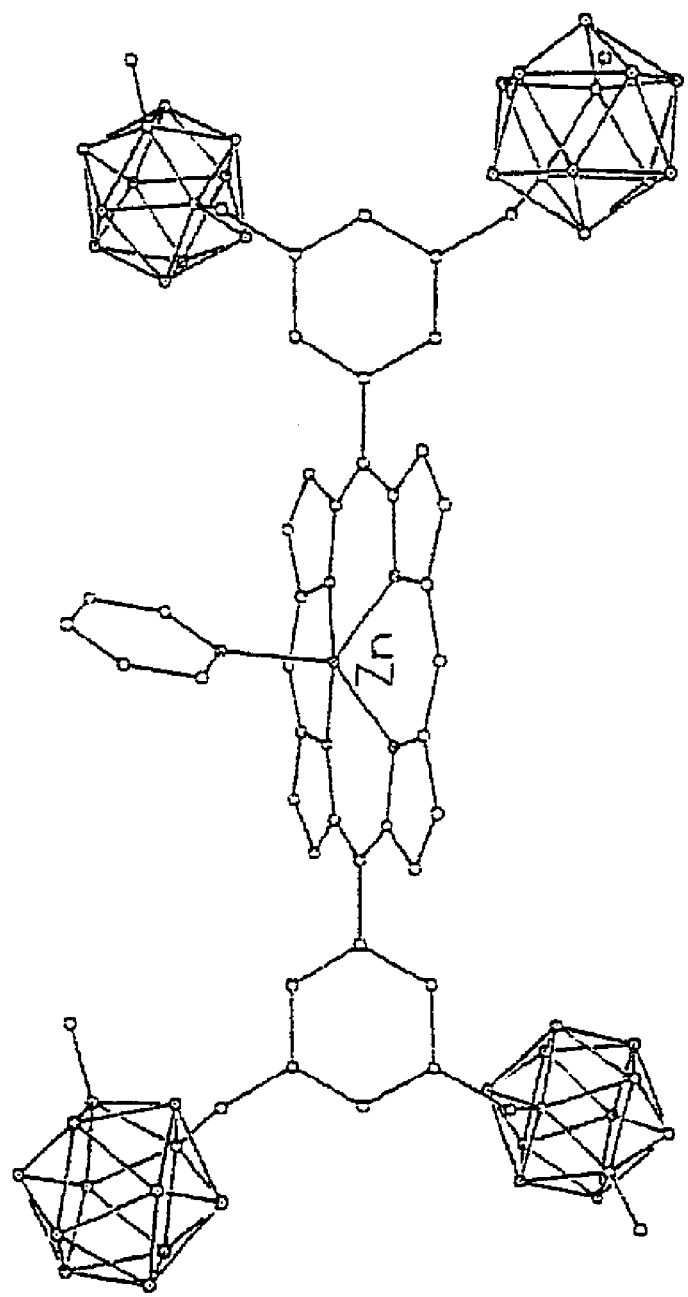
FIG. 12 depicts the structure inferred from X-ray data for compound 35 binding a pyridine molecule axially.
Figure 13A:
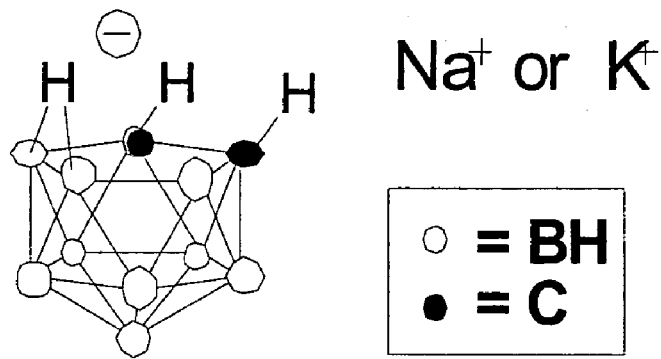
FIG. 13(a) depicts a nido-carborane group.
Figure 13B:
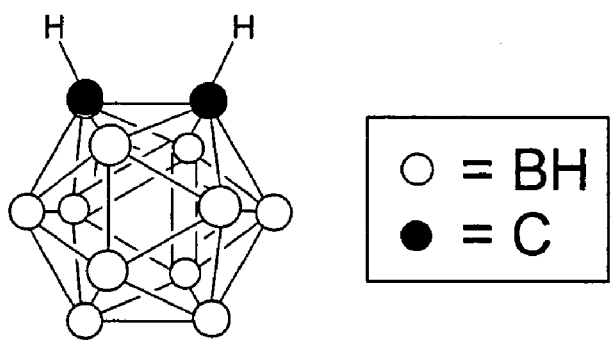
FIG. 13(b) depicts a closo-carborane group.
Figure 13C:
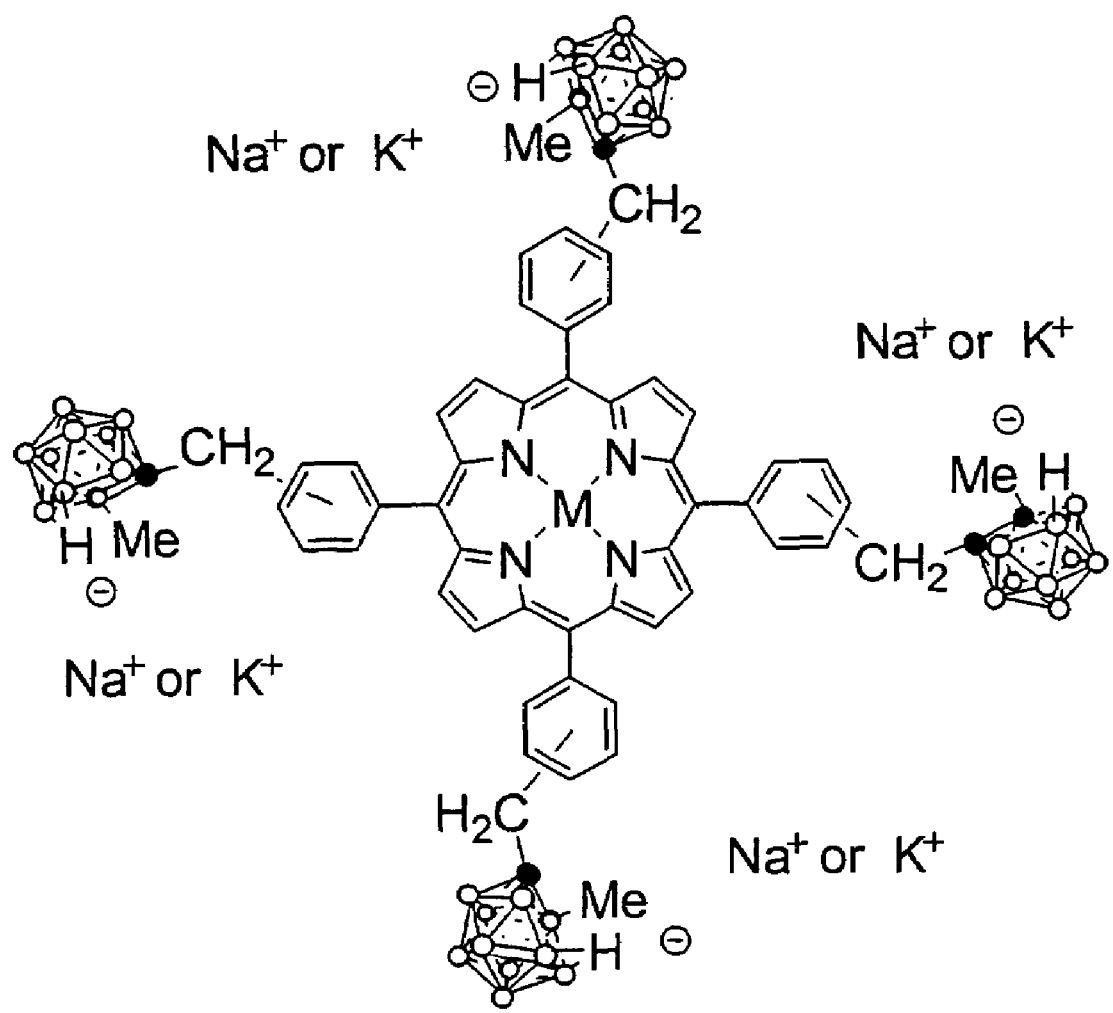
FIGS. 13(c)-(e) depict examples of active compounds.
Figure 13D:
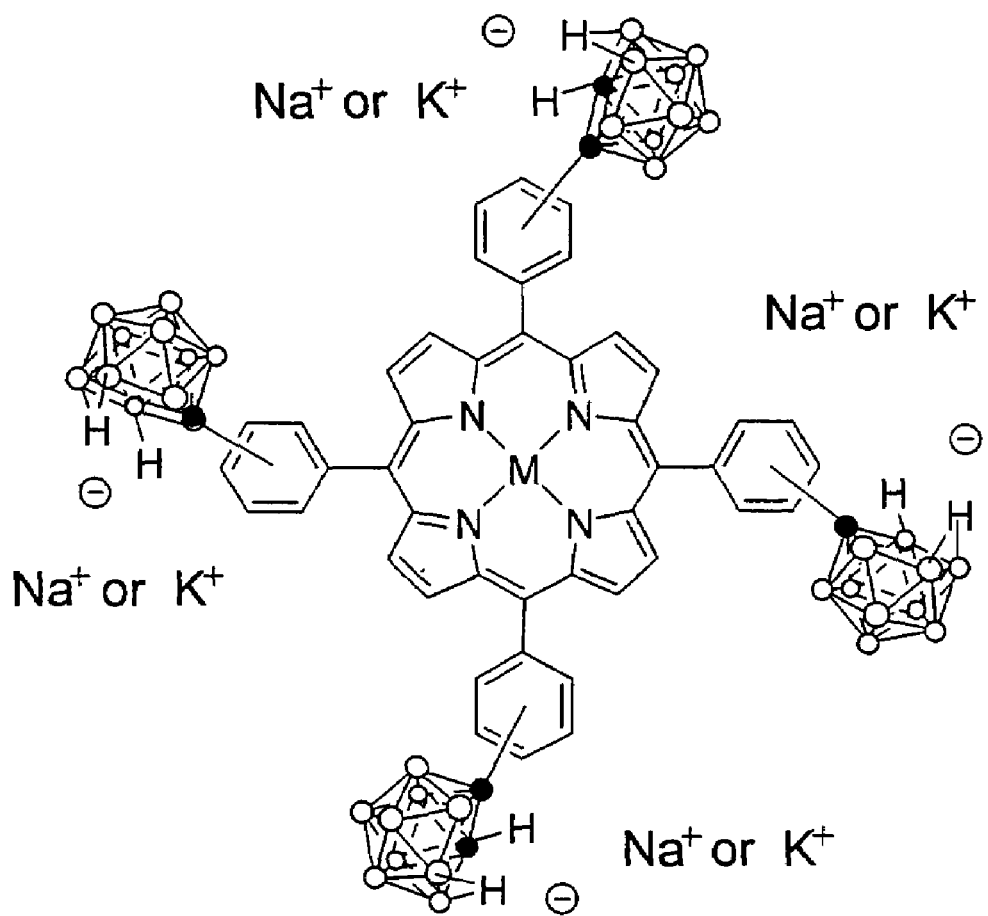
Figure 13E:
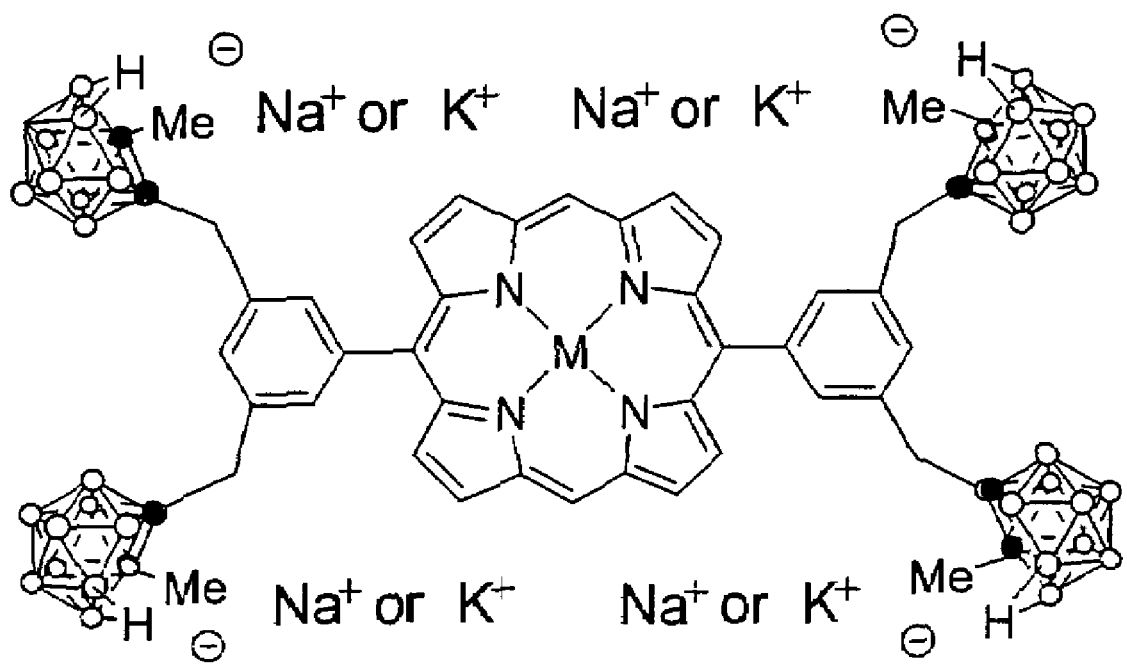

The binding of several compounds to various ligands has been tested, and some of the resulting bound complexes have been examined in the solid state by X-ray diffraction. FIG. 7 depicts the structure inferred from the X-ray data for compound 5 binding a methanol molecule axially. FIG. 8 depicts the structure inferred from the X-ray data for compound 17 binding a water molecule axially. FIG. 9 depicts the structure inferred from the X-ray data for compound 28 binding two chloride ions axially. FIG. 10 depicts the structure inferred from the X-ray data for compound 28 binding oxygen atoms from two picrate ions axially. FIG. 11 depicts the structure inferred from the X-ray data for compound 30 binding a pyridine molecule axially. FIG. 12 depicts the structure inferred from the X-ray data for compound 35 binding a pyridine molecule axially. The binding of pyridine, methanol, and biomolecules has also been examined in solution using UV-visible and fluorescence spectroscopy.

Future Experiments

Future planned experiments include the following:

1) Determine the binding affinity and binding kinetics for positively-charged molecules (e.g. pyridinium ions, bipyridinium ions, quaternary ammonium ions) to metal-free and metal-containing complexes of nido-carboranylporphyrins in solution. These studies will be followed by UV-Vis and fluorescence spectroscopy, mass spectrometry and nuclear magnetic resonance.
2) Determine the binding affinity and binding kinetics for neutral molecules (e.g. phenol, biphenols, amine-substituted molecules) to zinc and other metal-containing and metal-free complexes of nido- and closo-carboranylporphyrins in solution. These studies will be followed by UV-Vis and fluorescence spectroscopy, mass spectrometry and nuclear magnetic resonance.
3) Determine the binding affinity and binding kinetics of negatively-charged molecules (e.g. halides, phosphates, carboxylates) to metal-free or metal-containing, protonated or unprotonated, nido- and closo-carboranylporphyrins in solution. These studies will be followed by UV-Vis and fluorescence spectroscopy, mass spectrometry and nuclear magnetic resonance.

The complete disclosures of all references cited in this specification are hereby incorporated by reference. Also incorporated by reference are the complete disclosures of the following two provisional applications: Vicente and Marzilli, "Treating and preventing viral infections with porphyrin-based compounds," U.S. provisional patent application Ser. No. 60/426,062, filed Nov. 13, 2002; and Vicente, "Chelation of charged and uncharged molecules with porphyrin-based compounds," U.S. provisional patent application Ser. No. 60/426,612, filed Nov. 15, 2002. In the event of an otherwise irreconcilable conflict, however, the present specification shall control.

I claim:

1. A method for selectively binding a neutral, positively-charged, or negatively-charged molecule, in solution or in the solid state, said method comprising contacting the molecule with a compound comprising a porphyrin macrocycle, and further comprising one or more carboranyl groups that are linked to the porphyrin macrocycle by carbon-carbon bonding; wherein said selective binding comprises one or more of the following steps (a) through (c):

(a) coordination to a pentacoordinated or hexacoordinated metal ion in the core of the porphyrin macrocycle; or
(b) electrostatic interaction with one or more carboranyl groups; or
(c) π-π interaction with the porphyrin macrocycle;

wherein the compound has structure I:

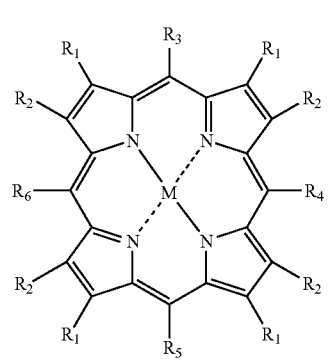

I wherein M is 2H or a pentacoordinated or hexacoordinated metal ion; R1 and R2 are each independently hydrogen, $C_1$ to $C_4$ alkyl or hydroxyalkyl; and R3, R4, R5, and R6 are each independently hydrogen, phenyl, or substituted phenyl having structure II:

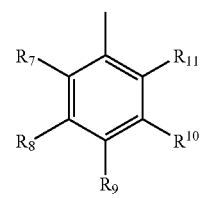

II wherein R7, R8, R9, R10, and R11 are independently hydrogen or a carboranyl group, wherein such a carboranyl group is linked to the phenyl group by a carbon-carbon bond; and wherein one or two of R7, R8, R9, R10, and R11 are such a carboranyl group;

wherein at least one of R3, R4, R5, and R6 is a substituted phenyl having structure II and having at least one such a carboranyl group; and wherein one or more of the following conditions (d) through (f) are satisfied:

(d) M is an iron(III), manganese(III), aluminum(III), or tin(IV) ion; or
(e) at least one of R3, R4, R5, and R6 is a substituted phenyl having structure II and having at least one such carboranyl group at R7 or R11; or
(f) at least one of the carboranyl groups is a closo-carboranyl group.

2. A method as recited in claim 1, wherein M is a zinc(II), iron(III), manganese(III), aluminum(III), or tin(IV) ion.

3. A method as recited in claim 1, wherein at least one of the carboranyl groups is a nido-carboranyl group.

4. A method as recited in claim 1, wherein at least one of the carboranyl groups is a closo-carboranyl group.

5. A method as recited in claim 1, wherein M is positively charged or protonated.

6. A method as recited in claim 1, wherein at least two of R3, R4, R5, and R6 are substituted phenyls having structure II and each having at least one such carboranyl group.

7. A method as recited in claim 1, wherein each of R3, R4, R5, and R6 is a substituted phenyl having structure II and each having at least one such carboranyl group.

8. A method as recited in claim 1, wherein at least two of R3, R4, R5, and R6 are substituted phenyls having structure II and each having at least one such nido-carboranyl group.

9. A method as recited in claim 1, wherein each of R3, R4, R5, and R6 is a substituted phenyl having structure II and each having at least one such closo-carboranyl group.

10. A method as recited in claim 1, wherein at least two of R3, R4, R5, and R6 are substituted phenyls having structure II and each having at least one such carboranyl group at R7 or R11.

11. A method as recited in claim 1, wherein each of R3, R4, R5, and R6 is a substituted phenyl having structure II and each having at least one such carboranyl group at R7 or R11.

12. A method as recited in claim 1, wherein at least two of R3, R4, R5, and R6 are substituted phenyls having structure II and each having at least one such carboranyl group at R8 or R10.

13. A method as recited in claim 1, wherein each of R3, R4, R5, and R6 is a substituted phenyl having structure II and each having at least one such carboranyl group at R8 or R10.

14. A method as recited in claim 1, wherein at least two of R3, R4, R5, and R6 are substituted phenyls having structure II and each having at least one such carboranyl group at R9.

15. A method as recited in claim 1, wherein each of R3, R4, R5, and R6 is a substituted phenyl having structure II and each having at least one such carboranyl group at R9.

16. A method as recited in claim 1, wherein the compound is selected from the group consisting of compounds 3, 5, 9, 11, 15, 17, 21, 23, 28, 30, 33, and 35, as depicted in FIGS. 1, 2, 3, 4, 5, and 6.

* * * * *